(12) United States Patent
Carter et al.

(10) Patent No.: US 7,754,721 B2
(45) Date of Patent: Jul. 13, 2010

(54) ARYLPIPERAZINE DERIVATIVES AND USES THEREOF

(75) Inventors: David Scott Carter, Sunnyvale, CA (US); Ryan Craig Schoenfeld, San Jose, CA (US); Robert James Weikert, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 376 days.

(21) Appl. No.: 11/893,943

(22) Filed: Aug. 17, 2007

(65) Prior Publication Data

US 2008/0045543 A1   Feb. 21, 2008

Related U.S. Application Data

(60) Provisional application No. 60/838,343, filed on Aug. 17, 2006.

(51) Int. Cl.
  *A61K 31/496*  (2006.01)
  *C07D 403/04*  (2006.01)
  *C07D 405/04*  (2006.01)
  *C07D 409/04*  (2006.01)
  *C07D 487/04*  (2006.01)

(52) U.S. Cl. ............... 514/252.11; 514/253.04; 514/253.05; 514/253.06; 514/253.09; 514/253.11; 544/362; 544/363; 544/364; 544/379

(58) Field of Classification Search .......... None
  See application file for complete search history.

(56) References Cited

U.S. PATENT DOCUMENTS 6,967,201 B1  11/2005  Briner et al.

FOREIGN PATENT DOCUMENTS

WO  WO 02/094799 A2  11/2002
WO  WO 03/015784 A1  2/2003
WO  WO 2004/080407 A2  9/2004
WO  2008/115593  *  9/2008

OTHER PUBLICATIONS

Boissier, J. R., et al., "N-Aryl-N'-(2-pyridylethyl) piperazines," *Chemical Abstract Service*, XP-002468143, 1963:462412, pp. 1-2.
Dorsey, J. M., et al. "Synthesis and Biological Evaluation of 2-(4-fluorophenoxy)-2-phenyl-ethyl Piperazines as Serotonin-selective Reuptake Inhibitors with a Potentially Improved Adverse Reaction Profile," *Bioorganic & Medicinal Chemistry*, 2004, vol. 12, pp. 1483-1491.
Fray, M. J., et al., "Structure-activity Relationships of N-substituted Piperazine Amine Reuptake Inhibitors," *Bioorganic & Medicinal Chemistry Letters*, 2006, vol. 16, pp. 4349-4353.

* cited by examiner

*Primary Examiner*—Emily Bernhardt
(74) *Attorney, Agent, or Firm*—Robert C. Hall

(57)   ABSTRACT

Compounds of the formula:

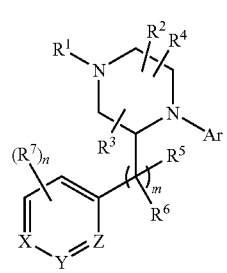

or pharmaceutically acceptable salts thereof,
wherein m, n, X, Y, Z, Ar, $R^1$, $R^2$, $R^3$, $R^4$, $R^5$, $R^6$ and $R^7$ are defined herein. Also provided are pharmaceutical compositions, methods of using, and methods of preparing the compounds.

19 Claims, No Drawings

ARYLPIPERAZINE DERIVATIVES AND USES THEREOF

CROSS-REFERENCE TO RELATED APPLICATIONS

This application claims the benefit of priority of U.S. Provisional Patent Application Ser. No. 60/838,343, filed on Aug. 17, 2006, the disclosure of which is incorporated herein by reference in its entirety.

FIELD OF THE INVENTION

This invention pertains to aryl- and heteroaryl-substituted piperazine compounds and methods for using the same. In particular, compounds of the present invention are useful for treatment of diseases associated with monoamine reuptake inhibitors.

BACKGROUND OF THE INVENTION

Monoamine deficiency has been long been linked to depressive, anxiolytic and other disorders (see, e.g.: Charney et al., *J. Clin. Psychiatry* (1998) 59, 1-14; Delgado et al., *J. Clin. Psychiatry* (2000) 67, 7-11; Resser et al., *Depress. Anxiety* (2000) 12 (Suppl 1) 2-19; and Hirschfeld et al., *J. Clin. Psychiatry* (2000) 61, 4-6. In particular, serotonin (5-hydroxytryptamine) and norepinephrine are recognized as key modulatory neurotransmitters that play an important role in mood regulation. Selective serotonin reuptake inhibitors (SSRIs) such as fluoxetine, sertraline, paroxetine, fluvoxamine, citalopram and escitalopram have provided treatments for depressive disorders (Masand et al., *Harv. Rev. Psychiatry* (1999) 7, 69-84). Noradrenaline or norepinephrine reuptake inhibitors such as reboxetine, atomoxetine, desipramine and nortryptyline have provided effective treatments for depressive, attention deficit and hyperactivity disorders (Scates et al., *Ann. Pharmacother.* (2000) 34, 1302-1312; Tatsumi et al., *Eur. J. Pharmacol.* (1997) 340, 249-258).

Enhancement of serotonin and norepinephrine neurotransmission is recognized to be synergistic in the pharmacotherapy of depressive and anxiolytic disorders, in comparison with enhancement of only serotonin or norepinephrine neurotransmission alone (Thase et al., *Br. J. Psychiatry* (2001) 178, 234, 241; Tran et al., *J. Clin. Psychopharmacology* (2003) 23, 78-86). Dual reuptake inhibitors of both serotonin and norepinephrine, such as duloxetine, milnacipran and venlafaxine are currently under development for treatment of depressive and anxiolytic disorders (Mallinckrodt et al., *J. Clin. Psychiatry* (2003) 5(1) 19-28; Bymaster et al., *Expert Opin. Investig. Drugs* (2003) 12(4) 531-543). Dual reuptake inhibitors of serotonin and norepinephrine also offer potential treatments for schizophrenia and other psychoses, dyskinesias, drug addition, cognitive disorders, Alzheimer's disease, obsessive-compulsive behaviour, attention deficit disorders, panic attacks, social phobias, eating disorders such as obesity, anorexia, bulimia and "binge-eating", stress, hyperglycaemia, hyperlipidemia, non-insulin-dependent diabetes, seizure disorders such as epilepsy, and treatment of conditions associated with neurological damage resulting from stroke, brain trauma, cerebral ischaemia, head injury and hemorrhage. Dual reuptake inhibitors of serotonin and norepinephrine also offer potential treatments for disorders and disease states of the urinary tract, and for pain and inflammation.

More recently, "triple reuptake" inhibitors ("broad-spectrum antidepressants" which inhibit the reuptake of norepinephrine, serotonin, and dopamine, have been recognized as useful for the treatment of depression and other CNS indications (Beer et al., *J. Clinical Pharmacology* (2004) 44:1360-1367; Skolnick et al., *Eur J Pharmacol*. (2003) February 14; 461(2-3):99-104.

There is accordingly a need for compounds that are effective as serotonin reuptake inhibitors, norepinephrine reuptake inhibitors, dopamine reuptake inhibitors, and/or dual reuptake inhibitors of serotonin, norepinephrine and/or dopamine, or triple reuptake inhibitors of norepinephrine, serotonin, and dopamine, as well as methods of making and using such compounds in the treatment of depressive, anxiolytic, genitourinary, pain, and other disorders. The present invention satisfies these needs.

SUMMARY OF THE INVENTION

One aspect of the invention provides compounds of formula I:

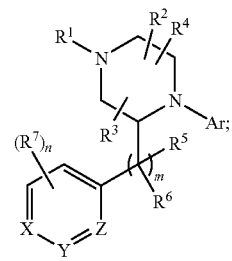

or a pharmaceutically acceptable salt thereof, wherein:
m is from 1 to 3;
n is from 0 to 2;
Ar is:
optionally substituted indolyl;
optionally substituted indazolyl;
optionally substituted azaindolyl;
optionally substituted azaindazolyl;
optionally substituted 2,3-dihydro-indolyl;
optionally substituted benzothiophenyl;
optionally substituted benzimidazolyl;
optionally substituted benzoxazolyl;
optionally substituted benzothiazolyl;
optionally substituted quinolinyl;
optionally substituted isoquinolinyl;
optionally substituted naphthalenyl; or
optionally substituted phenyl;
one of X, Y and Z is N and the others are $CR^a$, or X, Y and Z are $CR^a$ wherein:
each $R^a$ is independently hydrogen or $R^7$;
$R^1$ is: hydrogen; $C_{1-6}$alkyl; or an amine protecting group;
$R^2$, $R^3$ and $R^4$ each independently is hydrogen or $C_{1-6}$alkyl;
or $R^1$ together with one of $R^2$, $R^3$ and $R^4$ and the atoms to which they are attached may form a six-membered saturated ring;
or $R^2$ and one of $R^3$ and $R^4$ together with the atoms to which they are attached may form a six-membered saturated ring;
$R^5$ and $R^6$ each independently is hydrogen or $C_{1-6}$alkyl; and
each $R^7$ is independently:
$C_{1-6}$alkyl;
$C_{1-6}$alkyloxy;
hydroxy;

amino;
C$_{1-6}$alkylamino;
N,N-di-(C$_{1-6}$alkyl)-amino;
halo;
halo-C$_{1-6}$alkyl;
halo-C$_{1-6}$alkoxy;
hetero-C$_{1-6}$alkyl
C$_{1-6}$alkylsulfonyl;
C$_{1-6}$alkylsulfanyl;
cyano; or
—(CH$_2$)$_p$-A-C(O)—B—(CH$_2$)$_q$—R$^b$ wherein:
  p and q each independently is 0 or 1;
  A and B each independently is —O—, —NH— or a bond; and
  R$^b$ is;
    C$_{1-6}$alkyl;
    C$_{1-6}$alkyloxy;
    hydroxy;
    amino;
    C$_{1-6}$alkylamino;
    N,N-di-(C$_{1-6}$alkyl)-amino;
    halo-C$_{1-6}$alkyl;
    halo-C$_{1-6}$alkoxy; or
    hetero-C$_{1-6}$alkyl;

The invention also provides pharmaceutical compositions, methods of using, and methods of preparing the aforementioned compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. C$_1$-C$_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Amino means a moiety of the formula —NR—R' wherein R and R' each independently is hydrogen or alkyl as defined herein.

"Alkylamino means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminocarbonyl" means a group —C(O)—R wherein R is amino as defined herein.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —C(O)—R, where R' is alkyl as defined herein.

"Alkylsulfonyl" means a moiety of the formula —SO$_2$—R' where R' is alkyl as defined herein.

"Alkylsulfonylalkyl" means a moiety of the formula —R$^b$—SO$_2$—R$^a$, where R$^a$ is alkyl and R$^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylsulfonyloxy" means a moiety of the formula R$^a$—SO$_2$—O, where R$^a$ is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxolyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means a moiety of the formula —OR, wherein R is an aryl moiety as defined herein.

"Arylalkyl" and "Aralkyl", which may be used interchangeably, mean a radical-R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Azaindole" means a group of the formula

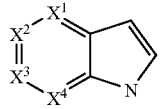

wherein one or two of any of $X^1$, $X^2$, $X^3$ and $X^4$ is N (aza), and the others are carbon. "Azaindoles" may be optionally substituted, as defined herein for heteroaryls, at position 1, 2 and 3, and at any of positions 4-through seven that are not nitrogen. "Azaindole" thus includes: "pyrrolopyrimidines" of the above formula wherein $X^2$ and $X^4$ are N; "pyrrolopyrimidines" of the above formula wherein $X^1$ and $X^3$ are N; "pyrrolopyrazines" of the above formula wherein $X^1$ and $X^4$ are N; "pyrrolopyridines" of the above formula wherein $X^1$ is N; "pyrrolopyridines" of the above formula wherein $X^2$ is N; "pyrrolopyridines" of the above formula wherein $X^3$ is N; and "pyrrolopyridines" of the above formula wherein $X^4$ is N.

"Azaindazole" means a group of the formula

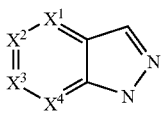

wherein one or two of any of $X^1$, $X^2$, $X^3$ and $X^4$ is N (aza), and the others are carbon. "Azaindazoles" may be optionally substituted, as defined herein for heteroaryls, at position 1, 2 and 3, and at any of positions 4-through seven that are not nitrogen. "Azaindaole" thus includes: "pyrazolopyrimidines" of the above formula wherein $X^2$ and $X^4$ are N; "pyrazolopyrimidines" of the above formula wherein $X^1$ and $X^3$ are N; "pyrazolopyrazines" of the above formula wherein $X^1$ and $X^4$ are N; "pyrazolopyridines" of the above formula wherein $X^1$ is N; "pyrazolopyridines" of the above formula wherein $X^2$ is N; "pyrazolopyridines" of the above formula wherein $X^3$ is N; and "pyrazolopyridines" of the above formula wherein $X^4$ is N.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R", where R' is alkylene and R" is cycloalkyl as defined herein.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" and "heteroaralkyl", which may be used interchangeably, mean a radical-$R^aR^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", "phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl)" or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, acylamino, mono-alkylamino, di-alkylamino, hydroxyalkyl, alkoxyalkyl, benzyloxy, cycloalkylalkyl, cycloalkoxy, cycloalkylalkoxy, alkylsulfonyloxy, optionally substituted thienyl, optionally substituted pyrazolyl, optionally substituted pyridinyl, morpholinocarbonyl, $-(CH_2)_q-S(O)_rR^f$; $-(CH_2)_q-NR^gR^h$; $-(CH_2)_q-C(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)-R^i$; $-(CH_2)_q-C(=O)-R^i$; or $-(CH_2)_q-N(R^f)-SO_2-R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy. Preferred optional substituents include alkyl, halo, haloalkyl, alkoxy, haloalkoxy, alkylsulfonyl, cyano, nitro, amino, aminocarbonyl and acetyl. Particularly preferred optional substituents include methyl, methoxy, methylamino, chloro, fluoro, cyano, aminocarbonyl, difluoromethoxy, trifluoromethyl, methanesulfonyl and aminomethyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disease states" associated with serotonin, norepinephrine and/or dopamine neurotransmission include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, haemorrhage, and disorders and disease states of the urinary tract. "Disease states" associated with serotonin, norepinephrine and/or dopamine neurotransmission also include inflammation conditions in a subject. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions.

"Depression" as used herein includes, but is not limited to, major depression, long-term depression, dysthymia, mental states of depressed mood characterised by feelings of sadness, despair, discouragement, "blues", melancholy, feelings of low self esteem, guilt and self reproach, withdrawal from interpersonal contact, and somatic symptoms such as eating and sleep disturbances.

"Anxiety" as used herein includes, but is not limited to, unpleasant or undesirable emotional states associated with psychophysiological responses to anticipation of unreal, imagined or exaggerated danger or harm, and physical concomitants such as increased heart rate, altered respiration rate, sweating, trembling, weakness and fatigue, feelings of impending danger, powerlessness, apprehension and tension.

"Disorders of the urinary tract" or "uropathy" used interchangeably with "symptoms of the urinary tract" means the pathologic changes in the urinary tract. Examples of urinary tract disorders include, but are not limited to, stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, $28^{th}$ Edition, W.B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention

The invention provides compounds of formula I:

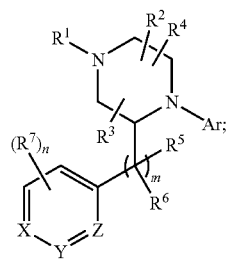

I or a pharmaceutically acceptable salt thereof, wherein:
m is from 1 to 3;
n is from 0 to 2;
Ar is:
optionally substituted indolyl;
optionally substituted indazolyl;
optionally substituted azaindolyl;
optionally substituted azaindazolyl;
optionally substituted 2,3-dihydro-indolyl;
optionally substituted benzothiophenyl;
optionally substituted benzimidazolyl;
optionally substituted benzoxazolyl;
optionally substituted benzothiazolyl;
optionally substituted quinolinyl;
optionally substituted isoquinolinyl;
optionally substituted naphthalenyl; or
optionally substituted phenyl;
one of X, Y and Z is N and the others are $CR^a$, or X, Y and Z are $CR^a$ wherein each $R^a$ is independently hydrogen or $R^7$;
$R^1$ is: hydrogen; $C_{1-6}$alkyl; or an amine protecting group;
$R^2$, $R^3$ and $R^4$ each independently is hydrogen or $C_{1-6}$alkyl;

or $R^1$ together with one of $R^2$, $R^3$ and $R^4$ and the atoms to which they are attached may form a six-membered saturated ring;

or $R^2$ and one of $R^3$ and $R^4$ together with the atoms to which they are attached may form a six-membered saturated ring;

$R^5$ and $R^6$ each independently is hydrogen or $C_{1-6}$alkyl; and each $R^7$ is independently:
$C_{1-6}$alkyl;
$C_{1-6}$alkyloxy;
hydroxy;
amino;
$C_{1-6}$alkylamino;
N,N-di-($C_{1-6}$alkyl)-amino;
halo;
halo-$C_{1-6}$alkyl;
halo-$C_{1-6}$alkoxy;
hetero-$C_{1-6}$alkyl
$C_{1-6}$alkylsulfonyl;
$C_{1-6}$alkylsulfanyl;
cyano; or
—$(CH_2)_p$-A-C(O)—B—$(CH_2)_q$—$R^b$ wherein:
p and q each independently is 0 or 1;
A and B each independently is —O—, —NH— or a bond; and
$R^b$ is;
$C_{1-6}$alkyl;
$C_{1-6}$alkyloxy;
hydroxy;
amino;
$C_{1-6}$alkylamino;
N,N-di-($C_{1-6}$alkyl)-amino;
halo-$C_{1-6}$alkyl;
halo-$C_{1-6}$alkoxy; or
hetero-$C_{1-6}$alkyl;

In certain embodiments the compounds of the invention are of formula Ia or formula Ib:

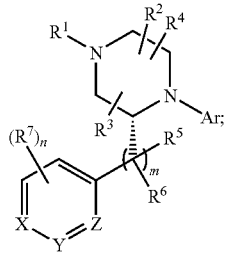

Ia

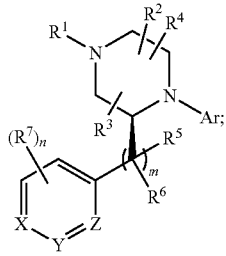

Ib wherein m, n, X, Y, Z, Ar, $R^1$, $R^2$, $R^3$, $R^4$, $R^5$, $R^6$ and $R^7$ are as defined herein.

In certain embodiments of formula I, Ia or Ib, X, Y and Z are $CR^a$.

In certain embodiments of formula I, Ia or Ib, m is 1.

In certain embodiments of formula I, Ia or Ib, Ar is: indolyl; indazolyl; azaindolyl; 2,3-dihydro-indolyl; benzothiophenyl; quinolinyl; isoquinolinyl; naphthalenyl; or phenyl, each optionally substituted.

In certain embodiments of formula I, Ia or Ib, Ar is: indolyl; indazolyl; azaindolyl; azaindazolyl; 2,3-dihydro-indolyl; benzothiophenyl; quinolinyl; or isoquinolinyl.

In certain embodiments of formula I, Ia or Ib, Ar is: optionally substituted naphthalenyl; or optionally substituted phenyl.

In certain embodiments of formula I, Ia or Ib, Ar is: indolyl; indazolyl; azaindolyl; azaindazolyl; or 2,3-dihydro-indolyl, each optionally substituted.

In certain embodiments of formula I, Ia or Ib, Ar is optionally substituted indolyl.

In certain embodiments of formula I, Ia or Ib, Ar is optionally substituted indazolyl.

In certain embodiments of formula I, Ia or Ib, Ar is optionally substituted azaindolyl.

In certain embodiments of formula I, Ia or Ib, Ar is optionally substituted benzothiophenyl.

In certain embodiments of formula I, Ia or Ib, Ar is optionally substituted benzimidazolyl.

In certain embodiments of formula I, Ia or Ib, Ar is optionally substituted benzoxazolyl.

In certain embodiments of formula I, Ia or Ib, Ar is optionally substituted benzothiazolyl.

In certain embodiments of formula I, Ia or Ib, Ar is optionally substituted quinolinyl.

In certain embodiments of formula I, Ia or Ib, Ar is optionally substituted isoquinolinyl.

In certain embodiments of formula I, Ia or Ib, Ar is optionally substituted naphthalenyl.

In certain embodiments of formula I, Ia or Ib, Ar is optionally substituted 2,3-dihydro-indolyl.

In certain embodiments of formula I, Ia or Ib, Ar is optionally substituted azaindazolyl.

In certain embodiments of formula I, Ia or Ib, Ar is optionally substituted phenyl.

In certain embodiments of formula I, Ia or Ib, Ar is indol-4-yl, indol-5-yl or indol-6-yl, each optionally substituted.

In certain embodiments of formula I, Ia or Ib, Ar is indol-5-yl or indol-6-yl, each optionally substituted.

In certain embodiments of formula I, Ia or Ib, Ar is optionally substituted indol-5-yl.

In certain embodiments of formula I, Ia or Ib, Ar is optionally substituted indazol-5-yl.

In certain embodiments of formula I, Ia or Ib, Ar is optionally substituted benzothiophen-5-yl.

In certain embodiments of formula I, Ia or Ib, Ar is optionally substituted naphthalen-2-yl.

In certain embodiments of formula I, Ia or Ib, Ar is optionally substituted quinolin-6-yl.

In certain embodiments of formula I, Ia or Ib, Ar is optionally substituted isoquinolin-6-yl.

In certain embodiments of formula I, Ia or Ib, Ar is optionally substituted pyrrolo[2,3-b]pyridin-5-yl.

In certain embodiments of formula I, Ia or Ib, Ar is phenyl optionally substituted once or twice with halo, $C_{1-6}$alkoxy or cyano.

In certain embodiments of formula I, Ia or Ib, n is 0.

In certain embodiments of formula I, Ia or Ib, n is 1.

In certain embodiments of formula I, Ia or Ib, n is 0 or 1.

In certain embodiments of formula I, Ia or Ib, m is 1.

In certain embodiments of formula I, Ia or Ib, m is 2.

In certain embodiments of formula I, Ia or Ib, m is 1 and $R^5$ and $R^6$ are hydrogen.

In certain embodiments of formula I, Ia or Ib, m is 2 and $R^5$ and $R^6$ are hydrogen.

In certain embodiments of formula I, Ia or Ib, $R^5$ and $R^6$ are hydrogen.

In certain embodiments of formula I, Ia or Ib, $R^2$, $R^3$ and $R^4$ are hydrogen.

In certain embodiments of formula I, Ia or Ib, $R^1$ is hydrogen.

In certain embodiments of formula I, Ia or Ib, $R^1$, $R^2$, $R^3$ and $R^4$ are hydrogen.

In certain embodiments of formula I, Ia or Ib, $R^1$, $R^2$, $R^3$, $R^4$, $R^5$ and $R^6$ are hydrogen.

In certain embodiments of formula I, Ia or Ib, $R^1$, $R^2$, $R^3$, $R^4$, $R^5$ and $R^6$ are hydrogen and m is 1.

In certain embodiments of formula I, Ia or Ib, $R^1$, $R^2$, $R^3$, $R^4$, $R^5$ and $R^6$ are hydrogen, m is 1, and X, Y and Z are $CR^a$.

In certain embodiments of formula I, Ia or Ib, $R^1$, $R^2$, $R^3$, $R^4$, $R^5$ and $R^6$ are hydrogen, m is 1, X, Y and Z are $CR^a$ and each $R^a$ is hydrogen.

In certain embodiments of formula I, Ia or Ib, $R^1$, $R^2$, $R^3$, $R^4$, $R^5$ and $R^6$ are hydrogen, m is 1, X, Y and Z are $CR^a$, each $R^a$ is hydrogen and n is 0.

In certain embodiments of formula I, Ia or Ib, $R^1$, $R^2$, $R^3$, $R^4$, $R^5$ and $R^6$ are hydrogen, m is 1, X, Y and Z are $CR^a$, each $R^a$ is hydrogen, n is 0, and Ar is optionally substituted indol-5-yl.

In certain embodiments of formula I, Ia or Ib, $R^1$, $R^2$, $R^3$, $R^4$, $R^5$ and $R^6$ are hydrogen, m is 1, X, Y and Z are $CR^a$, each $R^a$ is hydrogen, n is 0, and Ar is optionally substituted indazol-5-yl.

In certain embodiments of the invention, the compounds are of formula II:

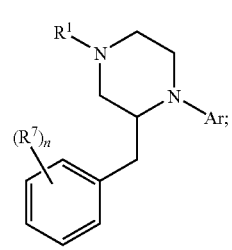

II wherein:
n is from 0 to 5; and
Ar, $R^1$ and $R^7$ are as defined herein.

In certain embodiments the compounds of the invention are of formula IIa or formula IIb:

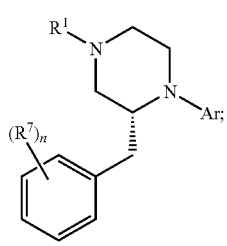

IIa

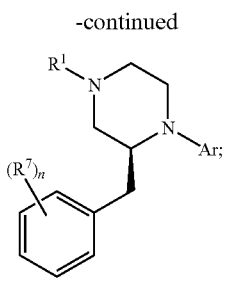

wherein:
n is from 0 to 5; and
Ar, $R^1$ and $R^7$ are as defined herein;

In certain embodiments of formula II, IIa or IIb, Ar is: indolyl; indazolyl; azaindolyl; 2,3-dihydro-indolyl; benzothiophenyl; quinolinyl; isoquinolinyl; naphthalenyl; or phenyl, each optionally substituted.

In certain embodiments of formula II, IIa or IIb, Ar is: indolyl; indazolyl; azaindolyl; azaindazolyl; 2,3-dihydro-indolyl; benzothiophenyl; quinolinyl; or isoquinolinyl.

In certain embodiments of formula II, IIa or IIb, Ar is: optionally substituted naphthalenyl; or optionally substituted phenyl.

In certain embodiments of formula II, IIa or IIb, Ar is: indolyl; indazolyl; azaindolyl; azaindazolyl; or 2,3-dihydro-indolyl, each optionally substituted.

In certain embodiments of formula II, IIa or IIb, Ar is optionally substituted indolyl.

In certain embodiments of formula II, IIa or IIb, Ar is optionally substituted indazolyl.

In certain embodiments of formula II, IIa or IIb, Ar is optionally substituted azaindolyl.

In certain embodiments of formula II, IIa or IIb, Ar is optionally substituted benzothiophenyl.

In certain embodiments of formula II, IIa or IIb, Ar is optionally substituted benzimidazolyl.

In certain embodiments of formula II, IIa or IIb, Ar is optionally substituted benzoxazolyl.

In certain embodiments of formula II, IIa or IIb, Ar is optionally substituted benzothiazolyl.

In certain embodiments of formula II, IIa or IIb, Ar is optionally substituted quinolinyl.

In certain embodiments of formula II, IIa or IIb, Ar is optionally substituted isoquinolinyl.

In certain embodiments of formula II, IIa or IIb, Ar is optionally substituted naphthalenyl.

In certain embodiments of formula II, IIa or IIb, Ar is optionally substituted 2,3-dihydro-indolyl.

In certain embodiments of formula II, IIa or IIb, Ar is optionally substituted azaindazolyl.

In certain embodiments of formula II, IIa or IIb, Ar is optionally substituted phenyl.

In certain embodiments of formula II, IIa or IIb, Ar is indol-4-yl, indol-5-yl or indol-6-yl, each optionally substituted.

In certain embodiments of formula II, IIa or IIb, Ar is indol-5-yl or indol-6-yl, each optionally substituted.

In certain embodiments of formula II, IIa or IIb, Ar is optionally substituted indol-5-yl.

In certain embodiments of formula II, IIa or IIb, Ar is optionally substituted indazol-5-yl.

In certain embodiments of formula II, IIa or IIb, Ar is optionally substituted benzothiophen-5-yl.

In certain embodiments of formula II, IIa or IIb, Ar is optionally substituted naphthalen-2-yl.

In certain embodiments of formula II, IIa or IIb, Ar is optionally substituted quinolin-6-yl.

In certain embodiments of formula II, IIa or IIb, Ar is optionally substituted isoquinolin-6-yl.

In certain embodiments of formula II, IIa or IIb, Ar is optionally substituted pyrrolo[2,3-b]pyridin-5-yl.

In certain embodiments of formula II, IIa or IIb, n is 0.
In certain embodiments of formula II, IIa or IIb, n is 1.
In certain embodiments of formula II, IIa or IIb, n is 0 or 1.
In certain embodiments of formula II, IIa or IIb, $R^1$ is hydrogen.

In certain embodiments of formula II, IIa or IIb, $R^1$, $R^2$, $R^3$ and $R^4$ are hydrogen.

In certain embodiments of formula II, IIa or IIb, $R^1$, $R^2$, $R^3$, $R^4$, $R^5$ and $R^6$ are hydrogen.

In certain embodiments of formula II, IIa or IIb, $R^1$ is hydrogen, and n is 0.

In certain embodiments of formula II, IIa or IIb, $R^1$ is hydrogen, n is 0, and Ar is optionally substituted indol-5-yl.

In certain embodiments of formula II, IIa or IIb, $R^1$ is hydrogen, n is 0, and Ar is optionally substituted indazol-5-yl.

In certain embodiments of the invention, the compounds are of formula III:

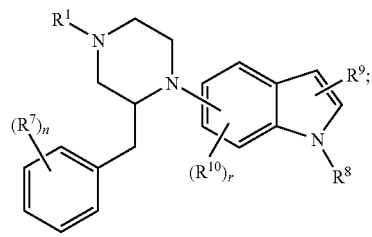

wherein:
n is from 0 to 5;
r is from 0 to 3;
$R^8$ is hydrogen or $C_{1-6}$alkyl;
$R^9$ and $R^{10}$ each is independently;
hydrogen;
$C_{1-6}$alkyl;
$C_{1-6}$alkyloxy;
hydroxy;
amino;
$C_{1-6}$alkylamino;
N,N-di-($C_{1-6}$alkyl)-amino;
halo;
halo-$C_{1-6}$alkyl;
halo-$C_{1-6}$alkoxy;
hetero-$C_{1-6}$alkyl
$C_{1-6}$alkylsulfonyl;
$C_{1-6}$alkylsulfanyl;
cyano; or
—$(CH_2)_p$-A-C(O)—B—$(CH_2)_q$—$R^b$;
p is 0 or 1;
q is 0 or 1;
A and B each independently is $NR^c$ or a bond, where $R^c$ is hydrogen or $C_{1-6}$alkyl;
$R^b$ is $C_{1-6}$alkyl, $C_{1-6}$alkoxy or amino; and
$R^1$ and $R^7$ are as defined herein.

In certain embodiments the compounds of the invention are of formula IIIa or formula IIIb:

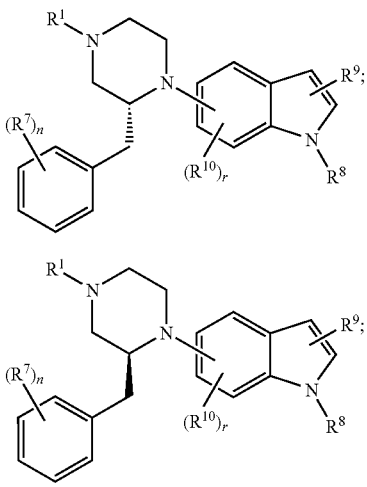

IIIa

IIIb wherein n, Ar, $R^1$ and $R^7$ are as defined herein.

In certain embodiments of the invention, the compounds are of formula IV:

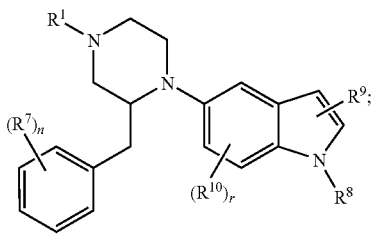

IV wherein n, r, $R^1$, $R^7$, $R^8$, $R^9$ and $R^{10}$ are as defined herein.

In certain embodiments the compounds of the invention are of formula IVa or formula IVb:

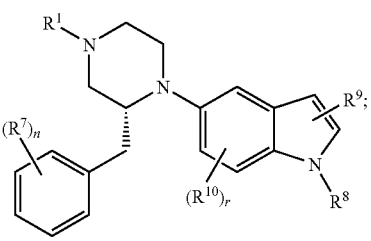

IVa

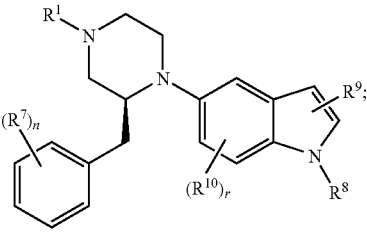

IVb wherein n, r, $R^1$, $R^7$, $R^8$, $R^9$ and $R^{10}$ are as defined herein.

In certain embodiments of the invention, the compounds are of formula V:

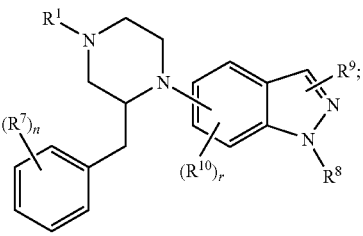

V wherein n, r, $R^1$, $R^7$, $R^8$, $R^9$ and $R^{10}$ are as defined herein.

In certain embodiments the compounds of the invention are of formula Va or formula Vb:

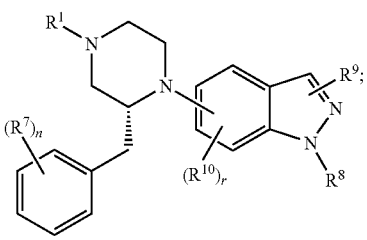

Va

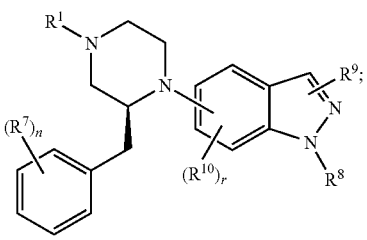

Vb wherein n, Ar, $R^1$ and $R^7$ are as defined herein.

In certain embodiments of the invention, the compounds are of formula IV:

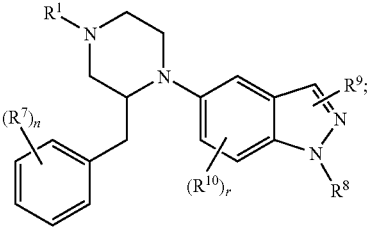

VI wherein n, r, $R^1$, $R^7$, $R^8$, $R^9$ and $R^{10}$ are as defined herein.

In certain embodiments the compounds of the invention are of formula VIa or formula VIb:

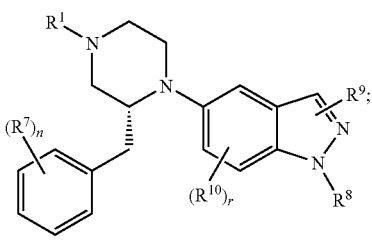

VIa

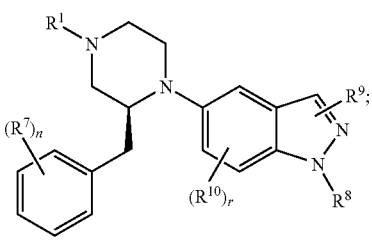

VIb wherein n, r, $R^1$, $R^7$, $R^8$, $R^9$ and $R^{10}$ are as defined herein.

In certain embodiments of the invention, the compounds are of formula VII:

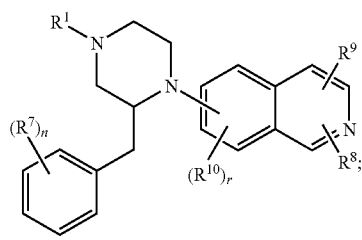

VII wherein n, r, $R^1$, $R^7$, $R^8$, $R^9$ and $R^{10}$ are as defined herein.

In certain embodiments the compounds of the invention are of formula VIIa or formula VIIb:

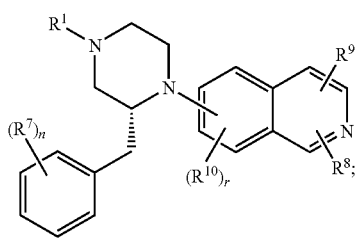

VIIa

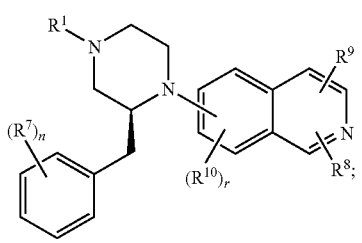

VIIb wherein n, Ar, $R^1$ and $R^7$ are as defined herein.

In certain embodiments of the invention, the compounds are of formula VIII:

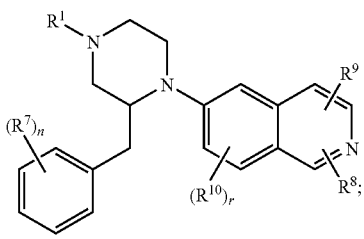

VIII wherein n, r, $R^1$, $R^7$, $R^8$, $R^9$ and $R^{10}$ are as defined herein.

In certain embodiments the compounds of the invention are of formula VIIIa or formula VIIIb:

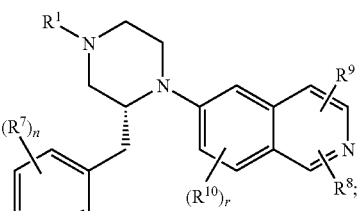

VIIIa

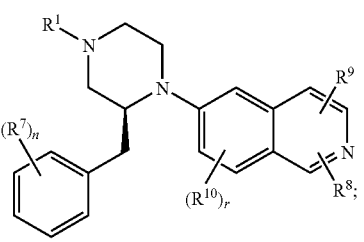

VIIIb wherein n, r, $R^1$, $R^7$, $R^8$, $R^9$ and $R^{10}$ are as defined herein.

In certain embodiments of any of formulas III, IIIa, IIIb, IV, IVa, IVb, V, Va, Vb, VI, VIa, VIb, VII, VIIa, VIIb, VIII, VIIIa, or VIIIb, $R^1$ is hydrogen.

In certain embodiments of any of formulas III, IIIa, IIIb, IV, IVa, IVb, V, Va, Vb, VI, VIa, VIb, VII, VIIa, VIIb, VIII, VIIIa, or VIIIb, $R^8$ is hydrogen.

In certain embodiments of any of formulas III, IIIa, IIIb, IV, IVa, IVb, V, Va, Vb, VI, VIa, VIb, VII, VIIa, VIIb, VIII, VIIIa, or VIIIb, $R^9$ is hydrogen.

In certain embodiments of any of formulas III, IIIa, IIIb, IV, IVa, IVb, V, Va, Vb, VI, VIa, VIb, VII, VIIa, VIIb, VIII, VIIIa, or VIIIb, $R^8$ is $C_{1-6}$alkyl.

In certain embodiments of any of formulas III, IIIa, IIIb, IV, IVa, IVb, V, Va, Vb, VI, VIa, VIb, VII, VIIa, VIIb, VIII, VIIIa, or VIIIb, r is 0.

In certain embodiments of any of formulas III, IIIa, IIIb, IV, IVa, IVb, V, Va, Vb, VI, VIa, VIb, VII, VIIa, VIIb, VIII, VIIIa, or VIIIb, r is 1.

In certain embodiments of any of formulas III, IIIa, IIIb, IV, IVa, IVb, V, Va, Vb, VI, VIa, VIb, VII, VIIa, VIIb, VIII, VIIIa, or VIIIb, $R^1$ is hydrogen.

In certain embodiments of any of formulas III, IIIa, IIIb, IV, IVa, IVb, V, Va, Vb, VI, VIa, VIb, VII, VIIa, VIIb, VIII, VIIIa, or VIIIb, r is 0 or 1.

In certain embodiments of any of formulas III, IIIa, IIIb, IV, IVa, IVb, V, Va, Vb, VI, VIa, VIb, VII, VIIa, VIIb, VIII, VIIIa, or VIIIb, r is 0 or 1 and $R^{10}$ is halo, cyano or $C_{1-6}$alkoxy.

In certain embodiments of any of formulas III, IIIa, IIIb, IV, IVa, IVb, V, Va, Vb, VI, VIa, VIb, VII, VIIa, VIIb, VIII, VIIIa, or VIIIb, $R^9$ is halo, cyano, alkyl, alkoxy or —C(O)—$NH_2$.

In certain embodiments of any of formulas III, IIIa, IIIb, IV, IVa, IVb, V, Va, Vb, VI, VIa, VIb, VII, VIIa, VIIb, VIII, VIIIa, or VIIIb, n is 0.

In certain embodiments of any of formulas III, IIIa, IIIb, IV, IVa, IVb, V, Va, Vb, VI, VIa, VIb, VII, VIIa, VIIb, VIII, VIIIa, or VIIIb, n is 0, and $R^1$ is hydrogen.

In certain embodiments of any of formulas III, IIIa, IIIb, IV, IVa, IVb, V, Va, Vb, VI, VIa, VIb, VII, VIIa, VIIb, VIII, VIIIa, or VIIIb, n is 0, $R^1$ is hydrogen, $R^8$ is hydrogen, and $R^9$ is hydrogen.

In certain embodiments of any of formulas III, IIIa, IIIb, IV, IVa, IVb, V, Va, Vb, VI, VIa, VIb, VII, VIIa, VIIb, VIII, VIIIa, or VIIIb, n is 0, $R^1$ is hydrogen, $R^8$ is hydrogen, $R^9$ is hydrogen, and r is 0 or 1.

In certain embodiments of any of formulas III, IIIa, IIIb, IV, IVa, IVb, V, Va, Vb, VI, VIa, VIb, VII, VIIa, VIIb, VIII, VIIIa, or VIIIb, n is 0, $R^1$ is hydrogen, $R^8$ is hydrogen, $R^9$ is hydrogen, r is 0 or 1, and $R^{10}$ is halo, $C_{1-6}$alkoxy or cyano.

Where any of $R^1$, $R^2$, $R^3$, $R^4$, $R^5$, $R^6$, $R^7$, $R^8$, $R^9$, $R^{10}$ or $R^a$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the methods of the invention are shown in Table 1.

TABLE 1

| # | Structure | Name | M + H |
|---|---|---|---|
| 1 | 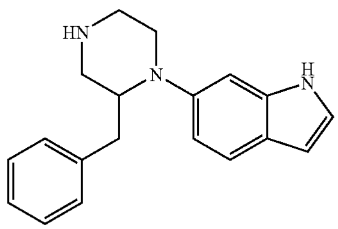 | 6-(2-Benzyl-piperazin-1-yl)-1H-indole | 292 |
| 2 | 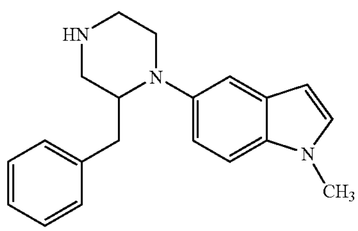 | 5-(2-Benzyl-piperazin-1-yl)-1-methyl-1H-indole | 306 |
| 3 | 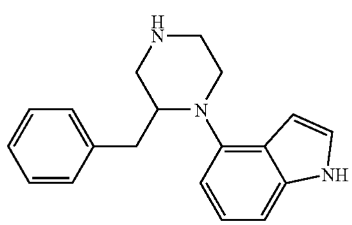 | 4-(2-Benzyl-piperazin-1-yl)-1H-indole | 292 |
| 4 | 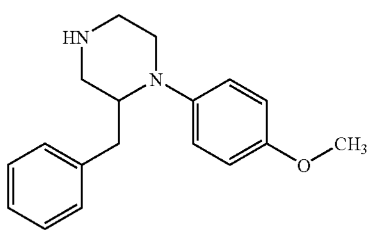 | 2-Benzyl-1-(4-methoxy-phenyl)-piperazine | 283 |
| 5 | 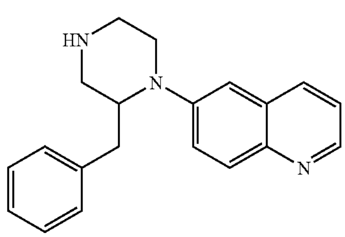 | 6-(2-Benzyl-piperazin-1-yl)-quinoline | 304 |

TABLE 1-continued
| # | Structure | Name | M + H |
|---|---|---|---|
| 6 | 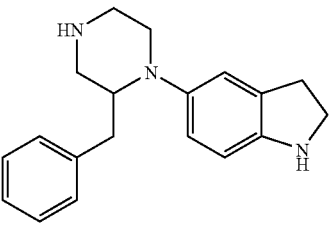 | 5-(2-Benzyl-piperazin-1-yl)-2,3-dihydro-1H-indole | 294 |
| 7 | 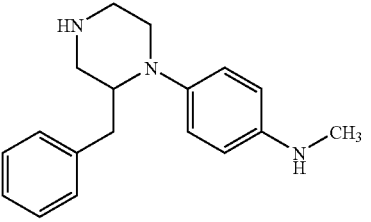 | [4-(2-Benzyl-piperazin-1-yl)-phenyl]-methyl-amine | 282 |
| 8 | 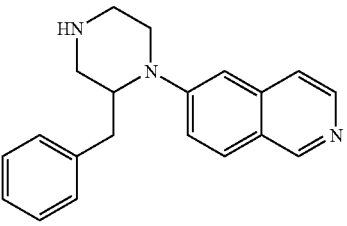 | 6-(2-Benzyl-piperazin-1-yl)-isoquinoline | 304 |
| 9 | 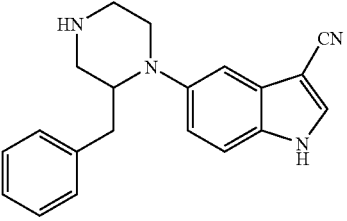 | 5-(2-Benzyl-piperazin-1-yl)-1H-indole-3-carbonitrile | 317 |
| 10 | 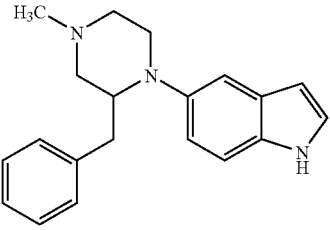 | 5-(2-Benzyl-4-methyl-piperazin-1-yl)-1H-indole | 306 |
| 11 | 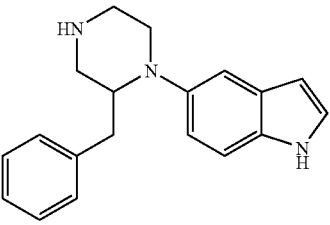 | 5-(2-Benzyl-piperazin-1-yl)-1H-indole | 292 |

TABLE 1-continued

| # | Structure | Name | M + H |
|---|---|---|---|
| 12 | 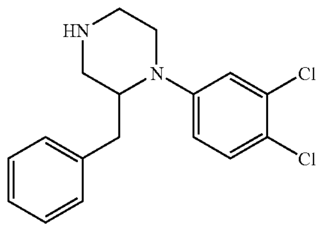 | 2-Benzyl-1-(3,4-dichloro-phenyl)-piperazine | 321 |
| 13 | 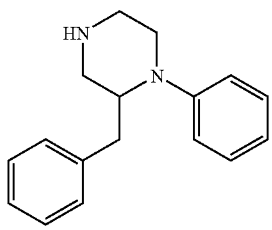 | 2-Benzyl-1-phenyl-piperazine | 253 |
| 14 | 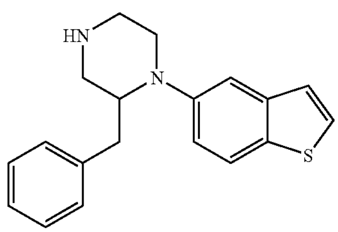 | 1-Benzo[b]thiophen-5-yl-2-benzyl-piperazine | 309 |
| 15 | 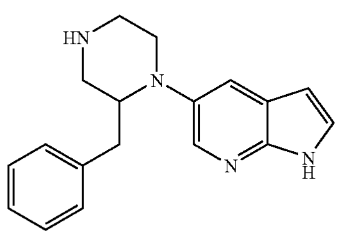 | 5-(2-Benzyl-piperazin-1-yl)-1H-pyrrolo[2,3-b]pyridine | 293 |
| 16 | 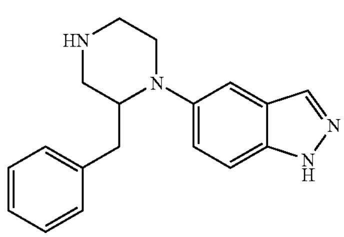 | 5-(2-Benzyl-piperazin-1-yl)-1H-indazole | 293 |
| 17 | 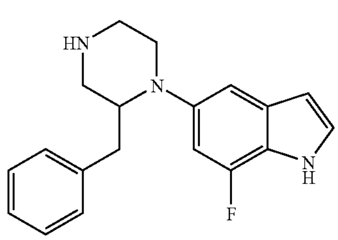 | 5-(2-Benzyl-piperazin-1-yl)-7-fluoro-1H-indole | 310 |

TABLE 1-continued

| # | Structure | Name | M + H |
|---|---|---|---|
| 18 | 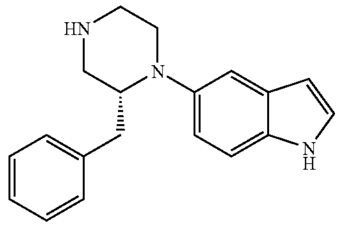 | (S)-5-(2-Benzyl-piperazin-1-yl)-1H-indole | 292 |
| 19 | 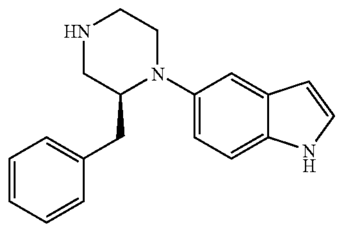 | (R)-5-(2-Benzyl-piperazin-1-yl)-1H-indole | 292 |
| 20 | 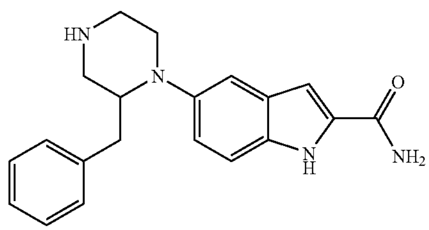 | 5-(2-Benzyl-piperazin-1-yl)-1H-indole-2-carboxylic acid amide | 335 |
| 21 | 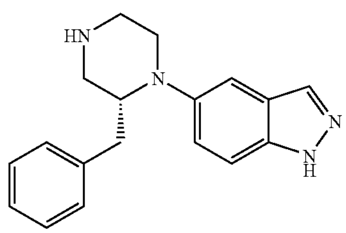 | (S)-5-(2-Benzyl-piperazin-1-yl)-1H-indazole | 293 |
| 22 | 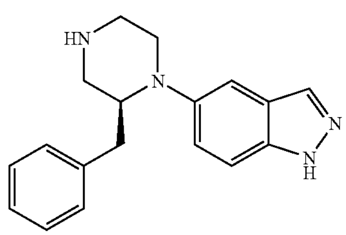 | (R)-5-(2-Benzyl-piperazin-1-yl)-1H-indazole | 293 |
| 23 | 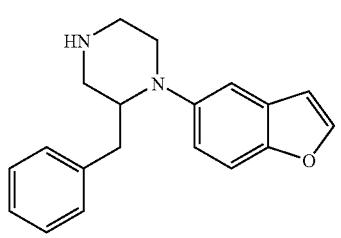 | 1-Benzofuran-5-yl-2-benzyl-piperazine | 293 |

TABLE 1-continued

| # | Structure | Name | M + H |
|---|---|---|---|
| 24 | 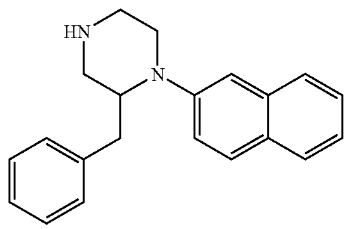 | 2-Benzyl-1-naphthalen-2-yl-piperazine | 303 |
| 25 | 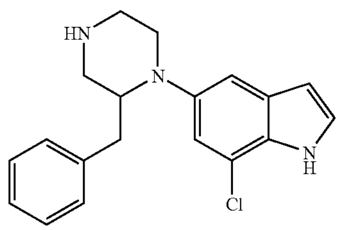 | 5-(2-Benzyl-piperazin-1-yl)-7-chloro-1H-indole | 326 |
| 26 | 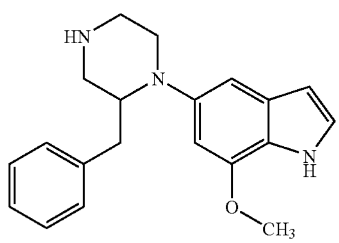 | 5-(2-Benzyl-piperazin-1-yl)-7-methoxy-1H-indole | 322 |
| 27 | 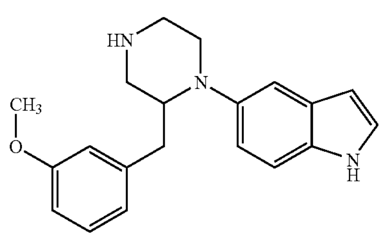 | 5-[2-(3-Methoxy-benzyl)-piperazin-1-yl]-1H-indole | 322 |
| 28 | 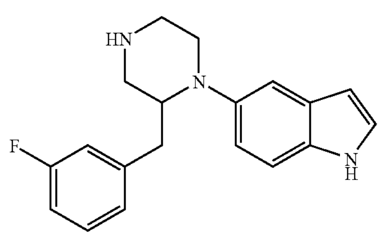 | 5-[2-(3-Fluoro-benzyl)-piperazin-1-yl]-1H-indole | 310 |
| 29 | 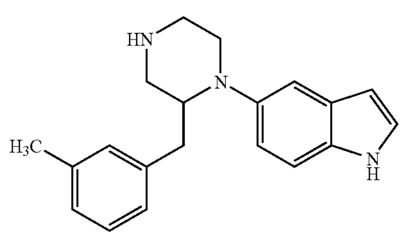 | 5-[2-(3-Methyl-benzyl)-piperazin-1-yl]-1H-indole | 306 |

TABLE 1-continued

| # | Structure | Name | M + H |
|---|---|---|---|
| 30 | 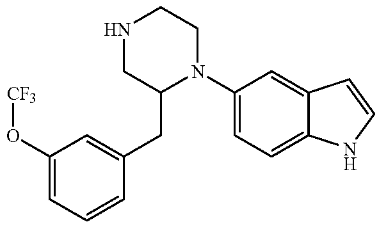 | 5-[2-(3-Trifluoromethoxy-benzyl)-piperazin-1-yl]-1H-indole | 376 |
| 31 | 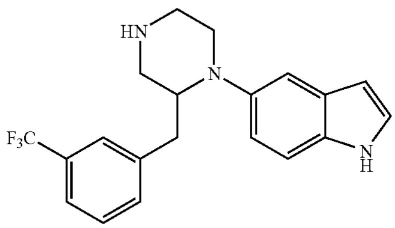 | 5-[2-(3-Trifluoromethyl-benzyl)-piperazin-1-yl]-1H-indole | 360 |
| 32 | | 5-[2-(4-Methoxy-benzyl)-piperazin-1-yl]-1H-indole | 322 |
| 33 | 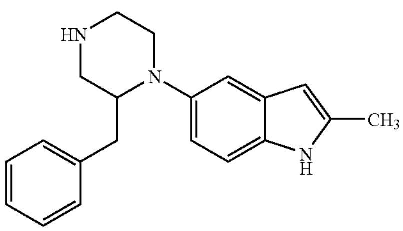 | 5-(2-Benzyl-piperazin-1-yl)-2-methyl-1H-indole | 306 |
| 34 | 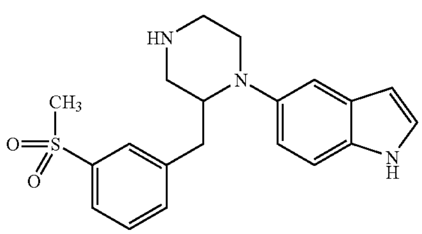 | 5-[2-(3-Methanesulfonyl-benzyl)-piperazin-1-yl]-1H-indole | 370 |
| 32 | | 5-[2-(2-Methoxy-benzyl)-piperazin-1-yl]-1H-indole | 322 |

TABLE 1-continued
| # | Structure | Name | M + H |
|---|---|---|---|
| 33 | 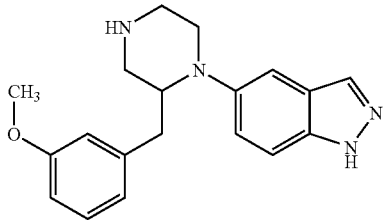 | 5-[2-(3-Methoxy-benzyl)-piperazin-1-yl]-1H-indazole | 323 |
| 34 | 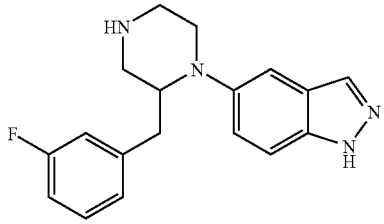 | 5-[2-(3-Fluoro-benzyl)-piperazin-1-yl]-1H-indazole | 311 |
| 35 | 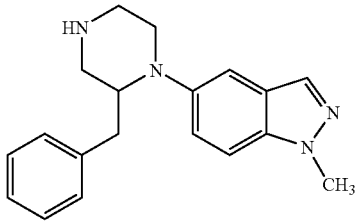 | 5-(2-Benzyl-piperazin-1-yl)-1-methyl-1H-indazole | 307 |
| 36 | 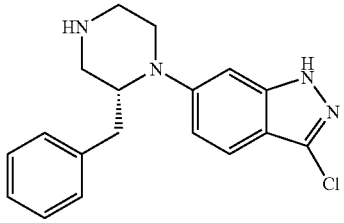 | (S)-6-(2-Benzyl-piperazin-1-yl)-3-chloro-1H-indazole | 327 |
| 37 | 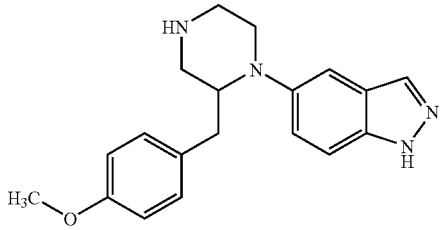 | 5-[2-(4-Methoxy-benzyl)-piperazin-1-yl]-1H-indazole | 323 |
| 38 | 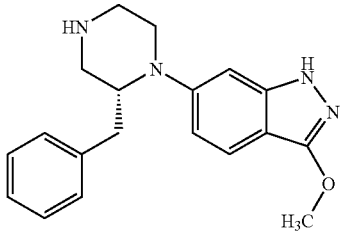 | (S)-6-(2-Benzyl-piperazin-1-yl)-3-methoxy-1H-indazole | 323 |

TABLE 1-continued

| # | Structure | Name | M + H |
|---|---|---|---|
| 39 | 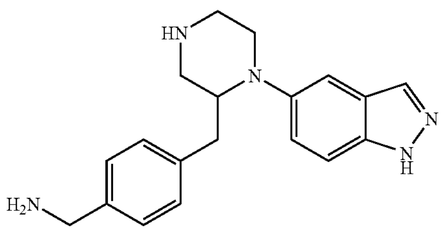 | 4-[1-(1H-Indazol-5-yl)-piperazin-2-ylmethyl]-benzylamine | 322 |
| 40 | 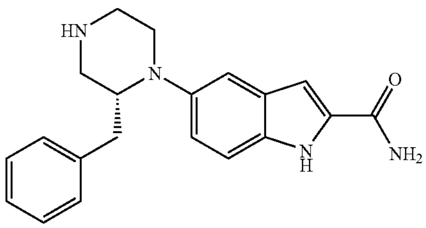 | (S)-5-(2-Benzyl-piperazin-1-yl)-1H-indole-2-carboxylic acid amide | 335 |
| 41 | 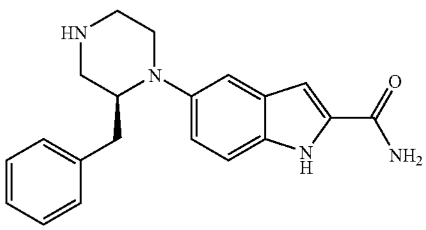 | (R)-5-(2-Benzyl-piperazin-1-yl)-1H-indole-2-carboxylic acid amide | 335 |
| 42 | 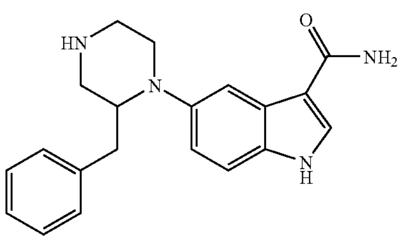 | 5-(2-Benzyl-piperazin-1-yl)-1H-indole-3-carboxylic acid amide | 335 |
| 43 | 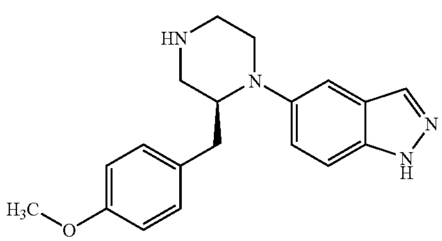 | (R)-5-[2-(4-Methoxy-benzyl)-piperazin-1-yl]-1H-indazole | 323 |
| 44 | 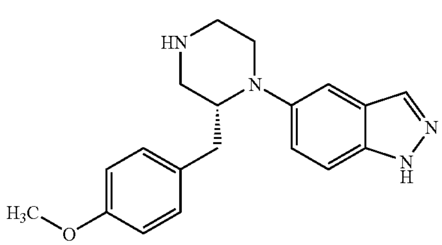 | (S)-5-[2-(4-Methoxy-benzyl)-piperazin-1-yl]-1H-indazole | 323 |

TABLE 1-continued

| # | Structure | Name | M + H |
|---|---|---|---|
| 45 | 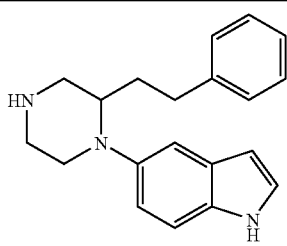 | 5-(2-Phenethyl-piperazin-1-yl)-1H-indole | 306 |
| 46 | 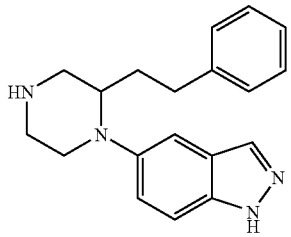 | 5-(2-Phenethyl-piperazin-1-yl)-1H-indazole | 307 |
| 47 | 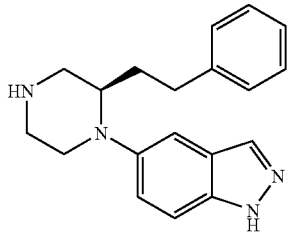 | (S)-5-(2-Phenethyl-piperazin-1-yl)-1H-indazole | 307 |
| 48 | 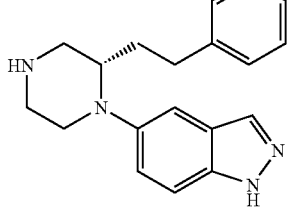 | (R)-5-(2-Phenethyl-piperazin-1-yl)-1H-indazole | 307 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. Scheme A below illustrates one synthetic procedure usable to prepare compounds of the invention, wherein PG is a protecting group and n, Ar, $R^1$, $R^2$, $R^3$, $R^4$, $R^5$, $R^6$ and $R^7$ are as defined herein.

SCHEME A

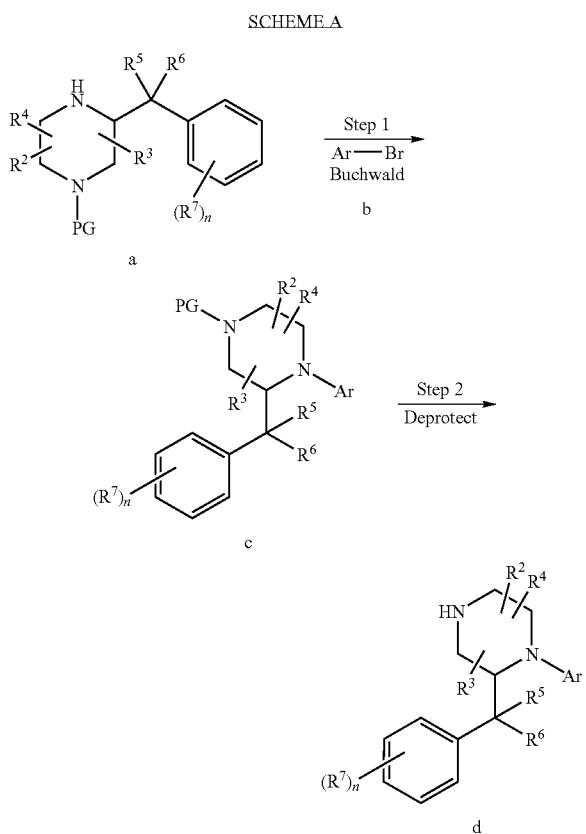

In Scheme A, aralkyl piperazine compound a is subject to Buchwald reaction with aryl bromide compound b using a palladium catalyst such as $PdCl_2[(o-Tol)_3P]_2$ or $Pd(OAc)_2$ together with trialkyl phospine or triaryl phosphine, to provide ayl piperazine compound c. Compound b may comprise, for example, a bromoindole, bromoindazole, bromobenzothiophene, bromoquinoline, bromoisoquinoline, bromonaphthalene, bromophenyl, or the like.

In step 2, aryl piperazine compound c may be deprotected to afford compound d. Compounds c and d are compounds of formula I in accordance with the invention.

In certain embodiments an additional step (not shown) may be carried out to alkylate the free secondary amine of piperazine compound d to provide compounds of formula I wherein $R^1$ is alkyl.

Numerous variations on the procedures of Scheme A are possible and will be readily apparent to those skilled in the art. Specific details for producing compounds of the invention are described in the Examples section below.

Utility

The compounds of the invention are usable for the treatment of diseases or conditions associated with serotonin neurotransmission, norepinephrine neuortransmission and/or dopamine neurotransmission. Such diseases and conditions include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, and haemorrhage.

The compounds of the invention are also usable for treatment of disorders and disease states of the urinary tract such as stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity.

The compounds of the invention also possess anti-inflammatory and/or analgesic properties in vivo, and accordingly, are expected to find utility in the treatment of disease states associated with pain conditions from a wide variety of causes, including, but not limited to, neuropathic pain, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Compounds of the invention are also useful for treatment of arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

| ABBREVIATIONS | |
|---|---|
| DCM | dichloromethane/methylene chloride |
| DMF | N,N-dimethylformamide |
| DMAP | 4-dimethylaminopyridine |
| EtOAc | ethyl acetate |
| EtOH | ethanol |
| tBuOH | tert-butanol |
| gc | gas chromatography |
| HMPA | hexamethylphosphoramide |
| hplc | high performance liquid chromatography |
| mCPBA | m-chloroperbenzoic acid |
| MeCN | acetonitrile |
| NMP | N-methyl pyrrolidinone |
| TEA | triethylamine |
| TFA | trifluoroacetic acid |
| THF | tetrahydrofuran |
| LDA | lithium diisopropylamine |
| LHMDS | Lithium bis(trimethylsilyl)amide |
| TBAF | tetrabutylammonium fluoride |
| TLC | thin layer chromatography |

Example 1

5-(2-Benzyl-piperazin-1-yl)-1H-indole

The synthetic procedure of this Example is outlined in Scheme C below.

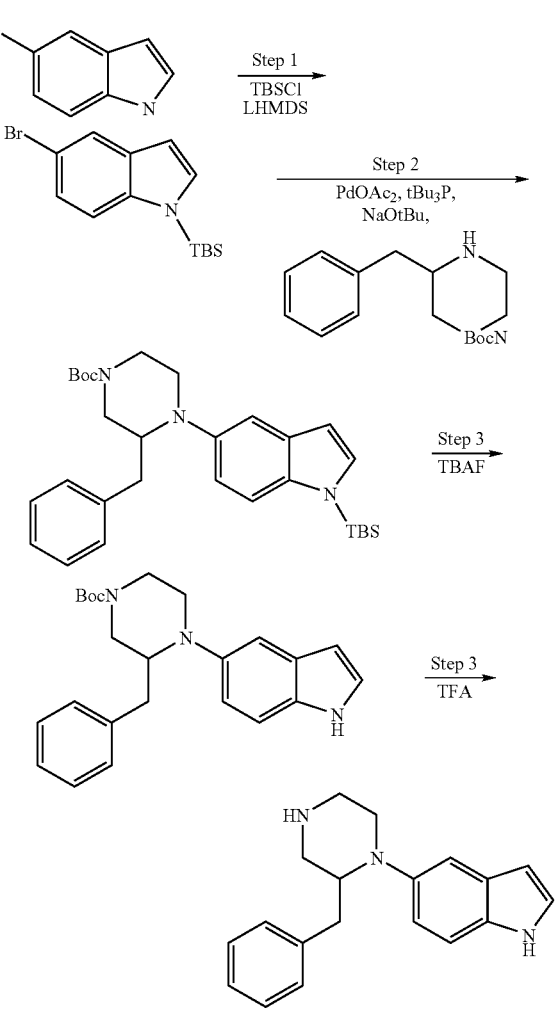

Step 1
5-Bromo-1-(tert-butyl-dimethyl-silanyl)-1H-indole

To a stirring solution of 5-bromo-indole (5.12 g, 26.1 mmol) in 130 mL THF at −78° C. was added LHMDS (28.7 mL, 1.0 M in THF, 28.7 mmol) drop-wise. During the addition the internal temperature was maintained below −60° C. The cooling bath was removed and the stirring solution was allowed to warm to room temperature. After 6 hours water was added, and the mixture was concentrated under reduced pressure, extracted with ethyl acetate and washed with $H_2O$ and brine. The combined organic layers were dried over $Na_2SO_4$, filtered and concentrated under reduced pressure. Purification via flash chromatography (gradient: 0 to 5% EtOAc in hexanes) afforded 5-bromo-1-(tert-butyl-dimethylsilanyl)-1H-indole (7.56 g, 98%) as a colorless oil; MS (M+H)=311.

Step 2 Benzyl-4-[1-(tert-butyl-dimethyl-silanyl)-1H-indol-5-yl]-piperazine-1-carboxylic acid tert-butyl ester To a mixture of Pd(OAc)$_2$ (0.054 g, 0.2 mmol), NaOtBu (0.64 g, 6.6 mmol) in xylene (7.0 mL) in a screw-capped tube was added tBu$_3$P (0.049 g, 0.2 mmol). After 10 minutes a solution of 5-bromo-1-(tert-butyl-dimethyl-silanyl)-1H-indole (1.30 g, 4.4 mmol) in xylene (7.0 mL) and a solution of 3-benzyl-piperazine-1-carboxylic acid tert-butyl ester (1.34 g, 4.8 mmol) in xylene (8.0 mL) were added. The mixture was heated to 80° C. for 30 minutes, then cooled to room temperature. The reaction mixture was taken up in ethyl acetate, filtered through a pad of celite, and concentrated under reduced pressure. Purification via flash chromatography (gradient: 2% to 20% EtOAc in hexane) afforded 3-Benzyl-4-[1-(tert-butyl-dimethyl-silanyl)-1H-indol-5-yl]-piperazine-1-carboxylic acid tert-butyl ester (1.65 g, 74%) as a pale yellow solid; MS (M+H)=506.

Step 3 3-Benzyl-4-(1H-indol-5-yl)-piperazine-1-carboxylic acid tert-butyl ester To a stirring solution of 3-benzyl-4-[1-(tert-butyl-dimethyl-silanyl)-1H-indol-5-yl]-piperazine-1-carboxylic acid tert-butyl ester (1.61 g, 3.2 mmol) in 20 mL THF at 0° C. was added TBAF (3.5 mL, 1.0 M in THF, 3.5 mmol). After 15 minutes the solution was quenched by the addition of water, concentrated under reduced pressure, and extracted with ethyl acetate. The combined organic layers were washed with water and brine, dried over Na$_2$SO$_4$, filtered and concentrated under reduced pressure. Purification via flash chromatography (5% to 40% EtOAc in hexanes) afforded 3-benzyl-4-(1H-indol-5-yl)-piperazine-1-carboxylic acid tert-butyl ester (1.17 g, 93%) as a white foam; MS (M+H)=392.

Step 4 5-(2-Benzyl-piperazin-1-yl)-1H-indole

To a stirring solution of 3-benzyl-4-(1H-indol-5-yl)-piperazine-1-carboxylic acid tert-butyl ester (0.309 g, 0.8 mmol) in 10 mL methylene chloride at 0° C. was added TFA (16.5 g, 80 mmol). The cooling bath was removed and the solution was stirred for 16 hours, then concentrated under reduced pressure, neutralized by addition saturated NaHCO$_3$, and extracted with ethyl acetate. The combined organic layers were dried over Na$_2$SO$_4$, filtered and concentrated under reduced pressure to afford a crude piperizine. Purification via flash chromatography (gradient: 8% to 80% of a mixture of DCM/MeOH/NH$_4$OH 60:10:1 in DCM) afforded 5-(2-benzyl-piperazin-1-yl)-1H-indole (0.17 g, 75%) as a yellow solid; $^1$H NMR (300 MHz, CDCl$_3$) δ 8.14 (bs, 1H), 7.36 (dt, J=8.7, 0.7 Hz, 1H), 7.31 (d, J=2.1 Hz, 1H), 7.26-7.03 (m, 7H), 6.51-6.49 (m, 1H), 3.6 (ddd, J=10.5, 8.2, 3.4 Hz, 1H), 3.26-2.94 (m, 6H), 2.86-2.71 (m, 2H), 2.67 (dd, J=13.1, 3.4 Hz, 1H); MS (M+H)=292.

Similarly, but omitting steps 1 and 3 and replacing 5-bromo-1-(tert-butyl-dimethyl-silanyl)-1H-indole with bromo-3,4-dichlorobenzene (0.42 g, 1.8 mmol) in step 2, 2-benzyl-1-(3,4-dichloro-phenyl)-piperazine (0.17 g) was prepared as an oil; $^1$H NMR (300 MHz, CDCl$_3$) δ 7.33-7.26 (m, 3H), 7.23-7.11 (m, 3H), 6.97 (d, J=2.9 Hz, 1H), 6.78 (dd, J=9.0, 2.9 Hz, 1H), 3.84-3.76 (m, 1H), 3.27-3.07 (m, 4H), 2.97-2.90 (m, 1H), 2.84 (ddd, J=12.2, 3.7, 1.1 Hz, 1H)), 2.60 (dd, J=13.1, 3.4 Hz, 1H), 1.55 (bs, 1H); MS (M+H)=322.

Similarly, but omitting steps 1 and 3 and replacing 5-bromo-1-(tert-butyl-dimethyl-silanyl)-1H-indole with bromobenzene (0.37 g, 2.4 mmol) in step 2, 2-benzyl-1-phenyl-piperazine (0.26 g) was made as an oil; $^1$H NMR (300 MHz, CDCl$_3$) δ 7.34-7.21 (m, 4H), 7.11-7.20 (m, 3H), 7.0-6.96 (m, 2H), 6.90-6.83 (m, 1H), 3.91-3.83 (m, 1H), 3.33-3.23 (m, 1H), 3.20-2.83 (m, 6H), 2.61 (dd, J=13.0, 3.2 Hz), 1.72 (bs, 1H); MS (M+H)=353.

Similarly, but omitting steps 1 and 3 and replacing 5-bromo-1-(tert-butyl-dimethyl-silanyl)-1H-indole with 5-bromo-benzo[b]thiophene (0.36 g, 1.7 mmol) in step 2, 1-Benzo[b]thiophen-5-yl-2-benzyl-piperazine (0.32 g) was afforded as a foam; $^1$H NMR (300 MHz, CDCl$_3$) δ 7.89 (d, J=8.8 Hz, 1H), 7.42 (d, J=15.4 Hz, 1H), 7.36 (d, J=2.5 Hz, 1H), 7.27-7.01 (m, 3H), 7.20-7.07 (m, 4H), 3.90-3.81 (m, 1H), 3.26-3.13 (m, 3H), 3.07-2.87 (m, 4H), 2.61 (dd, J=13.0, 3.1 Hz, 1H), 1.70 (bs, 1H); MS (M+H)=309.

Similarly, but replacing 5-bromo-1-1H-indole in step 1 with 5-bromo-1H-pyrrolo[2,3-b]pyridine (1.64 g, 8.3 mmol), 5-(2-Benzyl-piperazin-1-yl)-1H-pyrrolo[2,3-b]pyridine (0.14 g) was prepared as a pale yellow solid; $^1$H NMR (300 MHz, CDCl$_3$) δ 9.74 (bs, 1H), 8.26 (d, J=2.5 Hz, 1H), 7.69 (d, J=2.5 Hz, 1H), 7.33 (d, J=3.5 Hz, 1H), 7.26-7.10 (m, 3H), 7.07-7.03 (m, 2H), 6.46 (d, J=3.5 Hz, 1H), 3.64-3.54 (m, 1H), 3.27-2.97 (m, 5H), 2.86-2.73 (m, 2H), 2.65 (dd, J=13.2, 3.5 Hz, 1H); MS (M+H)=293.

Similarly, but replacing 5-bromo-1-1H-indole in step 1 with 5-bromo-7-fluoro-1H-indole (0.65 g, 3.1 mmol), 5-(2-Benzyl-piperazin-1-yl)-7-fluoro-1H-indole (0.22 g) was made as a white solid; $^1$H NMR (300 MHz, CDCl$_3$) δ 8.33 (bs, 1H), 7.27-7.04 (m, 6H), 7.03 (d, J=1.9 Hz, 1H), 6.80 (dd, J=13.5 Hz, 1.9 Hz, 1H), 3.64-3.56 (m, 1H), 3.25-2.80 (m, 7H), 2.66 (dd, J=13.1, 3.2 Hz, 1H), 2.0 (bs, 1H); MS (M+H)=310.

Similarly, but replacing 5-bromo-1-1H-indole in step 1 with 5-bromo-1H-indazole (1.03 g, 5.2 mmol), 5-(2-Benzyl-piperazin-1-yl)-1H-indazole (0.18 g) was prepared as a white foam; $^1$H NMR (300 MHz, DMSO-d$_6$) δ 12.81 (bs, 1H), 7.92 (s, 1H), 7.48 (d, J=9.0 H, 1H), 7.31-7.20 (m, 3H), 7.28-7.04 (m, 4H), 3.77-3.67 (m, 1H), 3.31 (bs, 1H), 3.07-3.96 (m, overlapping, 2H), 2.84-2.81 (m, 4H), 2.65 (dd, J=12.3, 2.8 Hz, 1H), 2.36 (dd, J=10.0, 3.0 Hz, 1H); MS (M+H)=293.

Similarly, but replacing 5-bromo-1-1H-indole in step 1 with 4-bromo-1H-indole (3.0 g, 15.3 mmol), 4-(2-Benzyl-piperazin-1-yl)-1H-indole (0.16) was provided as a white foam; $^1$H NMR (300 MHz, CDCl$_3$) δ 8.23 (bs, 1H), 7.21-7.07 (m, 6H), 7.00-6.93 (2H), 6.76 (d, J=6.7, 1.7 Hz, 1H), 6.62-6.57 (m, 1H), 4.03-3.91 (m, 1H), 3.54-3.41 (m, 1H), 3.23-3.03 (m, 4H), 2.95 (dd, J=13.1, 11.0 Hz, 1H), 2.85 (dd, J=13.1, 11.0, 1H), 2.64 (dd, J=13.2, 3.1 Hz, 1H); MS (M+H)=292.

Similarly, but replacing 5-bromo-1-1H-indole in step 1 with 6-bromo-1H-indole (0.50 g, 25.5 mmol), 6-(2-benzyl-piperazin-1-yl)-1H-indole (0.23 g) resulted as a colorless foam; $^1$H NMR (300 MHz, CDCl$_3$) δ 8.05 (bs, 1 h), 7.60 (d, J=9.4, 1H), 7.26-7.20 (m, 3H), 7.19-7.06 (m, 3H), 7.03-6.97 (m, 2H), 6.51-6.49 (m, 1H), 3.81-3.71 (m, 1H), 3.29-3.11 (m, 3H), 3.10-2.83 (m, 3H), 2.65 (dd, J=12.9, 2.9 Hz, 1H); MS (M+H)=292.

Similarly, but replacing 5-bromo-1-1H-indole in step 1 with 5-bromo-1-methyl-1H-indole (0.35 g, 1.7 mmol, prepared using the N-methylation described by Soll, Richard M. *Eur. J. Med. Chem. Chim Ther.* 1990, 25, 191), 5-(2-Benzyl-piperazin-1-yl)-1-methyl-1H-indole (0.28 g) was prepared, MS (M+H)=306.

Similarly, but omitting steps 1 and 3 and replacing 5-bromo-1-(tert-butyl-dimethyl-silanyl)-1H-indole with 4-Bromo-phenyl)-methyl-carbamic acid tert-butyl ester (0.46 g, 1.6 mmol) in step 2, [4-(2-Benzyl-piperazin-1-yl)-phenyl]-methyl-amine (0.05 g) was prepared; $^1$H NMR (300, MHz, CDCl$_3$) δ 7.24-7.13 (m, 3H), 7.06-6.99 (m, 4H), 6.65 (d, J=8.7, 1H), 3.62-3.50 (m, 1H), 3.26-3.12 (m, overlapping, 2H), 3.08 (dd, overlapping, J=12.5, 2.8 Hz, 1H), 2.91-2.73 (m, overlapping, 2H), 2.83 (s, overlapping, 3H), 2.51 (dd, J=13.8, 10.8 Hz, 1H); MS (M+H)=282.

Similarly, but omitting steps 1 and 3 and replacing 5-bromo-1-(tert-butyl-dimethyl-silanyl)-1H-indole with 1-bromo-4-methoxy-benzene (0.30 g, 1.6 mmol) in step 2, 2-benzyl-1-(4-methoxy-phenyl)-piperazine was prepared; $^1$H NMR (300, MHz, DMSO-d$_6$) δ 8.34 (bs, 1H), 7.43-7.36 (m, 2H), 7.35-7.13 (m, 3H), 7.07 (d, J=9.1 Hz, 2H), 6.93 (d, J=9.1 Hz, 2H), 3.90-3.80 (m, 1H), 3.73 (s, 3H), 3.33-3.06 (m, 5H), 3.00-2.90 (m, 1H), 2.80 (dd, J=15.4, 11.0 Hz, 1H), 2.53 (dd, J=15.4, 3.5 Hz, 1H); MS (M+H)=283.

Similarly, but omitting steps 1 and 3 and replacing 5-bromo-1-(tert-butyl-dimethyl-silanyl)-1H-indole with 6-bromo-quinoline (0.33 g, 1.6 mmol) in step 2, 6-(2-benzyl-piperazin-1-yl)-quinoline (0.18 g) was prepared; $^1$H NMR (300, MHz, CDCl$_3$) δ 8.81 (dd, J=4.3, 1.6 Hz, 1H), 8.10 (d, J=9.3 Hz, 1H), 8.07 (dd, J=7.3, 1.6 Hz, 1H), 7.56 (dd, J=9.2, 2.7 Hz, 1H), 7.40), 7.40 (dd, J=8.2, 4.2 Hz, 1H), 7.30-7.11 (m, 6H), 4.24-4.13 (m, 1H), 3.65-2.94 (m, 3H), 3.33-3.20 (m, 3H), 3.13 (dd, J=13.2, 11.0 Hz, 1H), 2.80 (dd, J=9.9, 4.4 Hz, 1H); MS (M+H)=304.

Similarly, but omitting steps 1 and 3 and replacing 5-bromo-1-(tert-butyl-dimethyl-silanyl)-1H-indole with 6-bromo-isoquinoline (0.33 g, 1.6 mmol) in step 2, 6-(2-benzyl-piperazin-1-yl)-isoquinoline (0.30 g) was prepared; $^1$H NMR (300, MHz, CDCl$_3$) δ 9.03 (s, 1H), 8.36 (d, J=5.9 Hz, 1H), 7.87 (d, J=9.2 Hz, 1H), 7.47 (d, J=5.9 Hz, 1H), 7.39 (dd, J=9.2, 2.4 Hz, 1H), 7.41-7.24 (m, 3H), 7.23-7.16 (m, 2H), 7.20 (d, J=2.2 Hz, 1H), 4.20-4.10 (m, 1H), 3.60-3.51 (m, 1H), 3.40-3.18 (m, 3H), 3.06-2.90 (m, 3H), 2.67 (dd, J=12.9, 4.0 Hz, 1H); MS (M+H)=304.

Similarly, but omitting steps 1 and 3 and replacing 5-bromo-1-(tert-butyl-dimethyl-silanyl)-1H-indole with 2-bromo-naphthalene (0.34 g, 1.6 mmol) in step 2, 2-benzyl-1-naphthalen-2-yl-piperazine (0.14 g) was prepared; $^1$H NMR (300 MHz, CDCl$_3$) δ 7.79 (d, J=9.0 Hz, 1H), 7.74 (d, overlapping, J=8.7 Hz, 1H), 7.72 (d, overlapping, J=8.0 Hz, 1H), 7.44-7.24 (m, 6H), 7.21-7.12 (m, 3H), 4.06-3.96 (m, 1H), 3.43-3.20 (m, 3H), 3.13 (dd, J=13.0, 10.9 Hz, 1H), 2.60 (dd, J=13.0, 3.2 Hz, 1H); MS (M+H)=303.

Similarly, but replacing 5-bromo-1-1H-indole in step 1 with 5-bromo-7-chloro-1H-indole (1.13 g, 4.9 mmol), 5-(2-benzyl-piperazin-1-yl)-7-chloro-1H-indole (0.10 g) was prepared; $^1$H NMR (300 MHz, CDCl$_3$) δ 8.25 (bs, 1H), 7.27-7.12 (m, 5H), 7.11-7.12 (m, 3H), 6.54 (dd, J=3.1, 2.1, 1H), 3.64-3.05 (m, 1H), 3.24-2.94 (m, 5H), 2.89-2.77 (m, 2H), 2.65 (dd, J=13.1, 3.1 Hz, 1H); MS (M+H)=326.

Similarly, but replacing 5-bromo-1-1H-indole in step 1 with 5-bromo-7-methoxy-1H-indole (0.50 g, 2.20 mmol), 5-(2-benzyl-piperazin-1-yl)-7-methoxy-1H-indole (0.17 g) was prepared; 1H NMR (300 MHz, CDCl$_3$) δ 8.28 (s, 1H), 7.25-7.19 (m, 2H), 7.18-7.11 (m, 2H), 7.09-7.04 (m, 2H), 6.93 (d, J=1.8 Hz, 1H), 6.55 (d, J=1.8 Hz, 1H), 6.48 (dd, J=3.6, 1.8 Hz, 1H), 3.97 (s, 3H), 3.63-3.54 (m, 1H), 3.27-2.98 (m, 5H), 2.88-2.67 (m, 3H); MS (M+H)=322.

Additional compounds prepared by the procedure of Example 1 are shown in Table 1.

Example 2

5-(2-Benzyl-4-methyl-piperazin-1-yl)-1H-indole

The synthetic procedure of this Example is outlined in Scheme D below.

SCHEME D

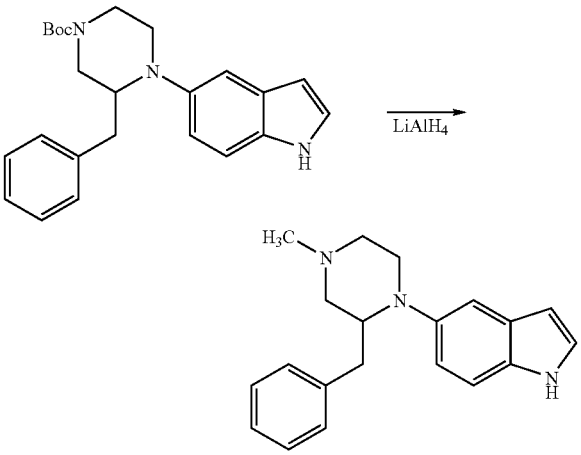

To a solution of 3-benzyl-4-(1H-indol-5-yl)-piperazine-1-carboxylic acid tert-butyl ester (0.39 g, 1.0 mmol) in 30 mL THF was added LiAlH$_4$ (2.5 mL, 1.0 M in THF). The solution was warmed to reflux for 2 hours, then cooled to room temperature and quenched by the slow addition of 50 mL saturated Rochelle's salt. The mixture was extracted with EtOA, and the combined organic layers were washed with brine, dried over MgSO$_4$, filtered and concentrated under reduced pressure to give an oil. Purification via flash chromatography (94:5:1 DCM/MeOH/NH$_4$OH) afforded 5-(2-benzyl-4-methyl-piperazin-1-yl)-1H-indole (0.21 g, 76%); $^1$H NMR (300, MHz, CDCl$_3$) δ 8.14 (bs, 1H), 7.37 (J=8.7 Hz, 1H), 7.31 (d, J=2.2 Hz, 1H), 7.26-7.05 (m, 1H), 6.52-6.49 (m, 1H), 3.64-3.71 (m, 1H), 3.31-3.21 (m, 1H), 3.20-3.11 (m, 1H), 2.82-2.70 (m, overlapping, 2H), 2.64 (dd, J=13.2, 7.7, 1H), 2.53-2.36 (m, 3H), 2.30 (s, 3H), MS (+H)=306).

Example 3

5-(2-Benzyl-piperazin-1-yl)-1H-indole-3-carbonitrile

The synthetic procedure of this Example is outlined in Scheme E below.

SCHEME E

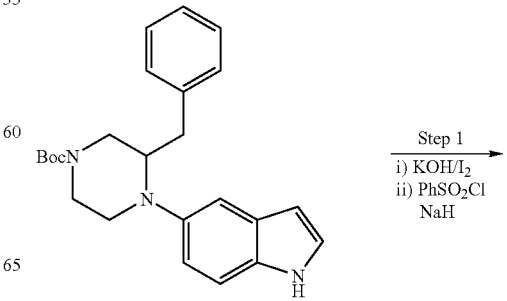

Step 1
i) KOH/I$_2$
ii) PhSO$_2$Cl
NaH

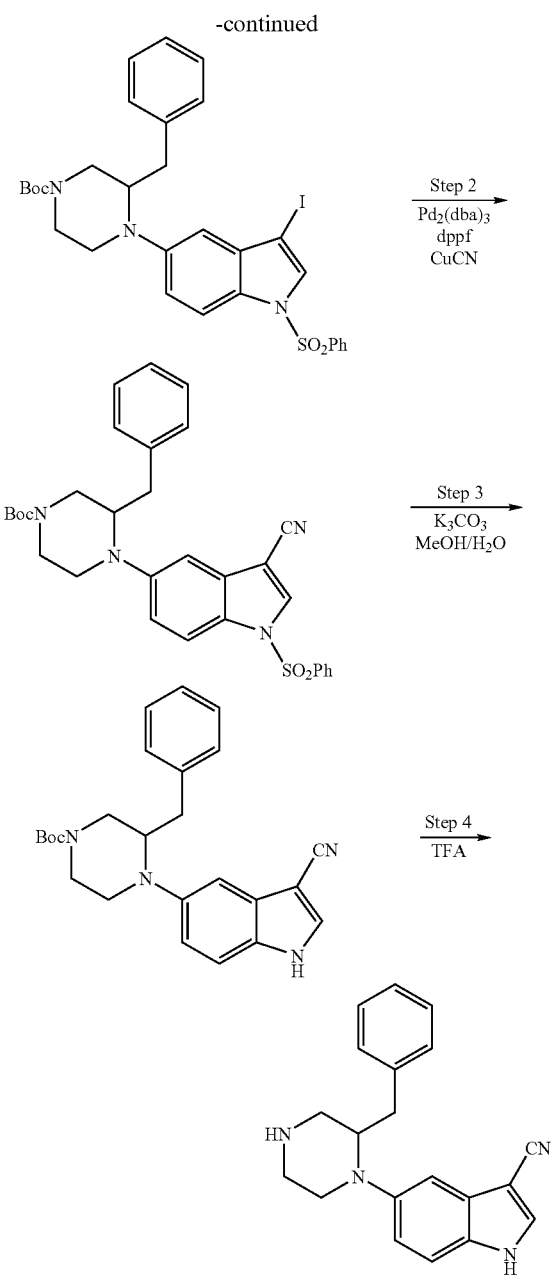

Step 1 4-(1-Benzenesulfonyl-3-iodo-1H-indol-5-yl)-3-benzyl-piperazine-1-carboxylic acid tert-butyl ester To a solution of 3-benzyl-4-(1H-indol-5-yl)-piperazine-1-carboxylic acid tert-butyl ester (0.17 g, 0.4 mmol) in 2.5 mL DMF was added powdered KOH (0.060 g, 1.1 mmol), followed by $I_2$ (0.11 g, 0.4 mmol) in DMF. The solution was stirred for 45 minutes and then treated with 10% aqueous $Na_2S_2O_3$. The mixture was extracted with EtOAc, and the combined organic layers were dried over $MgSO_4$, filtered, and concentrated under reduced pressure. The residue was immediately taken up in 2 mL DMF and treated with 60% NaH (0.02 g, 0.5 mmol). After 20 minutes the solution was treated with benzenesulfonyl chloride (0.07 mL, 0.5 mmol). After 30 minutes of stirring the mixture was quenched with $H_2O$ and extracted with EtOAc. The combined organic layers were washed with $H_2O$, washed with brine, dried over $MgSO_4$, filtered, and concentrated under reduced pressure. Purification via flash chromatography (30% EtOAc in hexanes) afforded 4-(1-benzenesulfonyl-3-iodo-1H-indol-5-yl)-3-benzyl-piperazine-1-carboxylic acid tert-butyl ester (0.23 g, 83%) as a white foam; MS (M+H)=658.

Step 2 4-(1-Benzenesulfonyl-3-cyano-1H-indol-5-yl)-3-benzyl-piperazine-1-carboxylic acid tert-butyl ester A mixture of 4-(1-benzenesulfonyl-3-iodo-1H-indol-5-yl)-3-benzyl-piperazine-1-carboxylic acid tert-butyl ester (0.23 g, 0.4 mmol), CuCN (0.13 g, 1.4 mmol), $Pd_2$(dibenzylideneacetone)$_3$ (0.017 g, 0.02 mmol), 1,1'-bis(diphenylphosphino)ferrocene (0.040 g, 0.07 mmol) was taken up in 5 mL 1,4 dioxane and warmed to reflux for one hour. The mixture was cooled to room temperature and filtered through a pad of celite. The filter cake was washed with EtOAc and the filtrate was concentrated under reduced pressure. Purification via flash chromatography (gradient: 15 to 25% EtOAc in hexanes) afforded 4-(1-benzenesulfonyl-3-cyano-1H-indol-5-yl)-3-benzyl-piperazine-1-carboxylic acid tert-butyl ester (0.20 g, 97%) as a white foam; MS (M+H)=557.

Step 3 3-Benzyl-4-(3-cyano-1H-indol-5-yl)-piperazine-1-carboxylic acid tert-butyl ester To a suspension of 4-(1-benzenesulfonyl-3-cyano-1H-indol-5-yl)-3-benzyl-piperazine-1-carboxylic acid tert-butyl ester (0.37 g, 0.7 mmol) in 10 mL MeOH was added $K_2CO_3$ (0.27 g, 2.0 mmol) in 2 mL $H_2O$. The reaction mixture was stirred for 30 minutes and then solution was concentrated under reduced pressure and extracted with EtOAc. The combine organic layers were dried over $MgSO_4$, filtered, and concentrated under reduced pressure. Purification via flash chromatography (25% EtOAc in hexane) afforded 3-benzyl-4-(3-cyano-1H-indol-5-yl)-piperazine-1-carboxylic acid tert-butyl ester (0.23 g, 85%) as a white foam; MS (M+H)=417.

Step 4 5-(2-Benzyl-piperazin-1-yl)-1H-indole-3-carbonitrile

The Boc group was removed from 3-benzyl-4-(3-cyano-1H-indol-5-yl)-piperazine-1-carboxylic acid tert-butyl ester using the procedure of step 4 of Example 1 to give 5-(2-benzyl-piperazin-1-yl)-1H-indole-3-carbonitrile (0.13 g, 76%) as a white foam. $^1$H NMR (300, MHz, CDCl$_3$) δ 8.57 (bs, 1H), 7.67 (d, J=2.7, Hz, 1H), 7.42 (d, J=8.9 Hz, 1H), 7.31-7.20 (m, 3H), 7.20-7.06 (m, 4H), 3.86-3.76 (m, 1H), 3.30-3.14 (m, 3H), 3.09-2.84 (m, 4H), 2.59 (dd, J=13.3, 3.5 Hz, 1H); MS (M+H)=317.

Example 4

5-(2-Benzyl-piperazin-1-yl)-2,3-dihydro-1H-indole

The synthetic procedure of this Example is outlined in Scheme G below.

SCHEME F

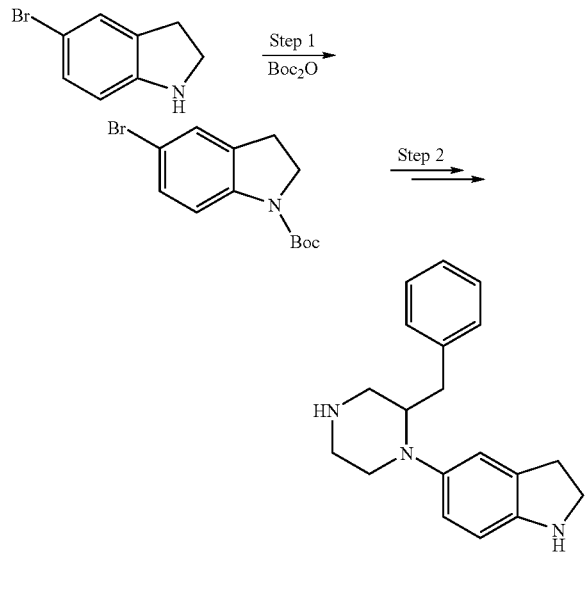

Step 1 5-Bromo-2,3-dihydro-indole-1-carboxylic acid tert-butyl ester

To a solution of 5-bromo-2,3-dihydro-1H-indole (2.11 g, 10.7 mmol) in 40 mL of THF was added Boc$_2$O (2.56 g, 11.7 mmol). The reaction mixture was stirred at room temperature for 18 hours, and then concentrated under reduced pressure. Purification of the residue via flash chromatography (8% EtOAc in hexane) afforded 5-bromo-2,3-dihydro-indole-1-carboxylic acid tert-butyl ester (2.59 g, 95%) as a white solid; MS (M+H)=298.

Step 2 5-(2-Benzyl-piperazin-1-yl)-2,3-dihydro-1H-indole

Following the procedure of steps 2 and 4 of Example 1, 5-bromo-2,3-dihydro-indole-1-carboxylic acid tert-butyl ester (0.48 g, 1.6 mmol) was coupled with 3-benzyl-piperazine-1-carboxylic acid tert-butyl ester to give 5-(2-benzyl-4-tert-butoxycarbonyl-piperazin-1-yl)-2,3-dihydro-indole-1-carboxylic acid tert-butyl ester, which was then deprotected by reaction with TFA to afford 5-(2-benzyl-piperazin-1-yl)-2,3-dihydro-1H-indole (0.16 g) as a yellow foam; $^1$H NMR (300, MHz, CDCl$_3$) δ 7.24-7.10 (m, 3H), 7.17-1.01 (m, 2H), 6.96 (d, J=2.2 Hz, 1H), 6.82 (dd, J=8.2, 2.2 Hz, 1H), 3.61-3.46 (m, 3H), 3.20-2.69 (m, 7H), 2.84-2.72 (m, 2H), 2.56 (dd, J=10.5, 13.6 Hz, 1H); MS (M+H)=294.

Example 5

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 6

Screening for Human Serotonin Transporter (hSERT) Antagonists Using a Scintillation Proximity Assay (SPA)

The screening assay of this example was used to determine the affinity of ligands at the hSERT transporter by competition with [$^3$H]-Citalopram.

Scintillation Proximity Assay (SPA) works by bringing radioligand within close proximity to the bead's scintillant to stimulate light emission. In this assay, the receptor-containing membranes were pre-coupled to the SPA beads and the binding of the appropriate radioligand to the transporter was measured. The light emission was proportional to the amount of bound radioligand. Unbound radioligand produced no signal as a result of distant proximity to scintillant (lack of energy transfer).

HEK-293 cells (Tatsumi et al., Eur. J. Pharmacol. 1997, 30, 249-258) stably expressing recombinant hSERT were maintained with media (DMEM high glucose with 10% FBS, 300 µg/ml G418 and 2 mM L-Glutamine) and incubated at 37° C. with 5% $CO_2$. Cells are released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3 mg/ml (w:v). and stored at −80° C.

For Scintillation Proximity Assay $IC_{50}/K_i$ determination, 50 mM Tris-HCl and 300 mM NaCl, (pH 7.4) buffers were utilized. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the [$^3$H]-Citalopram radioligand was added at 50 µl/well. Membrane and beads were prepared to a ratio of 10 µg:0.7 mg, with 0.7 mg PVT-WGA Amersham beads (Cat# RPQ0282V) added per well. 130 µl of the membrane:bead mixture was added to the assay plate. The mixtures were allowed to stand at room temperature for one hour, and were then counted on a Packard TopCount LCS, a generic Scintillation Proximity Assay counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound counts per minute (CPM) at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for human serotonin transporter. For example, 6-(2-Benzyl-piperazin-1-yl)-isoquinoline exhibited a pKi of approximately 9.87 using the above assay.

Example 7

Screening for Compounds Active at Human Norepinephrine Transporter (hNET) Using a Scintillation Proximity Assay (SPA)

This assay was used to determine the affinity of ligands for the hNET transporter by competition with [$^3$H]-Nisoxetine. As in the hSERT assay of the above example, receptor-containing membranes were pre-coupled to the SPA beads and the binding of the appropriate radioligand to the transporter was measured. The light emission was proportional to the amount of bound radioligand, with unbound radioligand producing no signal.

HEK-293 cells (Tatsumi et al., Eur. J. Pharmacol. 1997, 30, 249-258) stably expressing recombinant hNET (Clone: HEK-hNET #2) were maintained with media (DMEM hi glucose with 10% FBS, 300 µg/ml G418 and 2 mM L-Glutamine) and incubated at 37° C. with 5% $CO_2$. Cells were released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube ($7.5 \times 10^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3-6 mg/ml (w:v). and stored at −80° C.

$^3$[H] Nisoxetine radioligand (Amersham Cat. # TRK942 or Perkin Elmer Cat. # NET1084, specific activity: 70-87 Ci/mmol, stock concentration: 1.22e-5 M, final concentration: 8.25e-9 M), and 50 mM Tris-HCl, 300 mM NaCl, (pH 7.4) buffers were used for Scintillation Proximity Assay $IC_{50}$/$K_i$ determination. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the radioligand was added at 50 µl/well. Membrane and beads were prepared to a ratio of 10 µg:0.7 mg, with 0.7 mg PVT-WGA Amersham beads (Cat# RPQ0282V) added per well. 130 µl of the membrane: bead mixture was added to the assay plate. The mixtures were allowed to stand at room temperature for one hour, and were then counted on a Packard TopCount LCS, a generic SPA counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{max - min}{1 + (IC50/x)^n} + min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human norepinephrine transporter. For example, 5-(2-Benzyl-piperazin-1-yl)-7-fluoro-1H-indole exhibited a pKi of approximately 8.19 using the above assay.

Example 8

Screening for Compounds Active at Human Dopamine Transporter Using a Scintillation Proximity Assay (SPA)

This assay was used to determine the affinity of ligands for the dopamine transporter by competition with [$^3$H]-Vanoxerine.

HEK-293 cells (Tatsumi et al., Eur. J. Pharmacol. 1997, 30, 249-258) stably expressing recombinant hDAT were maintained with media (DMEM hi glucose with 10% FBS, 300 µg/ml G418 and 2 mM L-Glutamine) and incubated at 37° C. with 5% $CO_2$. Cells were plated four hours prior to experiment by placing approximately 30,000 cells per well (in PBS) on white, opaque Cell-Tak coated 96 well plates. Extra buffer was apriated from the cell plates using an ELx405 plate washer.

$^3$[H] vanoxerine (GBR 12909) radioligand, specific activity approximately 59 Ci/mmol, stock concentration, 400 nM, and 50 mM Tris-HCl, 300 mM NaCl, (pH 7.4) buffers were used for Scintillation Proximity Assay $IC_{50}$/$K_i$ determination. Compounds of the invention were diluted from 10 mM to 0.1 nM FAC (10 point curves, whole log/half log dilutions) via a Beckman Biomek 2000 using a 10-point dilution protocol. The mixtures were allowed to stand at room temperature for 30 minutes, and were then counted on a Packard TopCount LCS, a generic SPA counting protocol settings, Count Time (min.): 0.40, Background Subtract: none, Half-Life Correction: none, Quench Indicator: tSIS, Platemap blank subtraction: none, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{max - min}{1 + (IC50/x)^n} + min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human dopamine transporter. For example, 5-(2-Benzyl-piperazin-1-yl)-1H-indole-2-carboxylic acid amide exhibited a pKi of approximately 8.54 using the above assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present inven-

What is claimed is:

1. A compound of formula I:

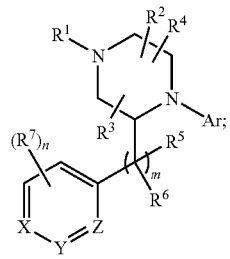

I or a pharmaceutically acceptable salt thereof,
wherein:
 m is from 1 to 3;
 n is from 0 to 2;
 Ar is:
  indolyl;
  indazolyl;
  azaindolyl;
  azaindazolyl;
  2,3-dihydro-indolyl;
  benzothiophenyl;
  quinolinyl; or
  isoquinolinyl;
  wherein Ar is may be substituted with chloro, fluoro, cyano, methyl, methoxy or —C(O)—NH$_2$;
 one of X, Y and Z is N and the others are CR$^a$, or X, Y and Z are CR$^a$ wherein each R$^a$ is independently hydrogen or R$^7$;
 R$^1$ is: hydrogen; or C$_{1-6}$alkyl;
 R$^2$, R$^3$ and R$^4$ each independently is hydrogen or C$_{1-6}$alkyl;
 R$^5$ and R$^6$ each independently is hydrogen or C$_{1-6}$alkyl; and
 each R$^7$ is independently:
  C$_{1-6}$alkyl;
  C$_{1-6}$alkyloxy;
  hydroxy;
  amino;
  C$_{1-6}$alkylamino;
  N,N-di-(C$_{1-6}$alkyl)-amino;
  halo;
  halo-C$_{1-6}$ alkyl;
  halo-C$_{1-6}$alkoxy;
  C$_{1-6}$alkylsulfonyl;
  C$_{1-6}$alkylsulfanyl;
  cyano; or
  —(CH$_2$)$_p$-A-C(O)—B—(CH$_2$)$_q$—R$^b$ wherein:
   p and q each independently is 0 or 1;
   A and B each independently is —O—, —NH— or a bond; and
   R$^b$ is;
    C$_{1-6}$alkyl;
    C$_{1-6}$alkyloxy;
    hydroxy;
    amino;
    C$_{1-6}$alkylamino;
    N,N-di-(C$_{1-6}$alkyl)-amino;
    halo-C$_{1-6}$alkyl; or
    halo-C$_{1-6}$alkoxy.

2. The compound of claim 1, wherein Ar is:
 indolyl;
 indazolyl;
 azaindolyl;
 azaindazolyl; or
 2,3-dihydro-indolyl.

3. The compound of claim 1, wherein Ar is indolyl.

4. The compound of claim 1, wherein Ar is indazolyl.

5. The compound of claim 1, wherein Ar is indol-4-yl, indol-5-yl, indol-6-yl, indol-5-yl or indol-6-yl.

6. The compound of claim 1, wherein Ar is indol-5-yl.

7. The compound of claim 1, wherein Ar is indazol-5-yl.

8. The compound of claim 1, wherein n is 0 or 1.

9. The compound of claim 8, wherein m is 1 or 2.

10. The compound of claim 9, wherein X, Y and Z are CR$^a$.

11. The compound of claim 10, wherein R$^5$ and R$^6$ are hydrogen.

12. The compound of claim 11, wherein R$^2$, R$^3$ and R$^4$ are hydrogen.

13. The compound of claim 12, wherein R$^1$ is hydrogen.

14. The compound of claim 1, wherein said compound is of formula II:

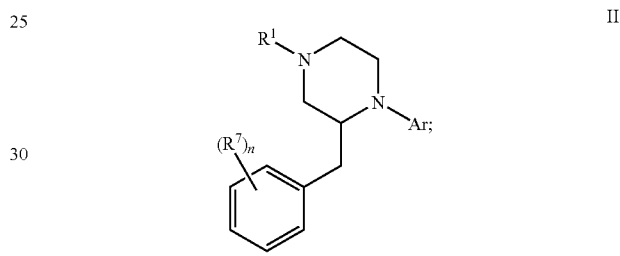

II wherein n, R$^1$ and R$^7$ are as recited in claim 1.

15. A compound of formula IV:

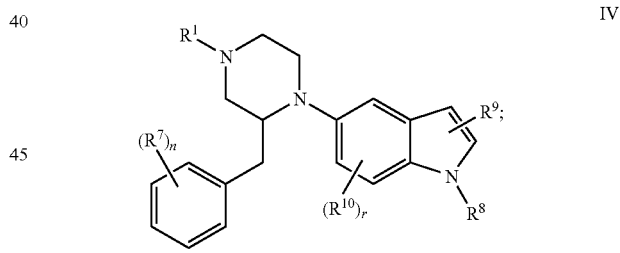

IV wherein:
 n is from 0 to 2;
 r is 0 or 1;
 R$^1$ is: hydrogen; or C$_{1-6}$alkyl;
 each R$^7$ is independently:
  C$_{1-6}$alkyl;
  C$_{1-6}$alkyloxy;
  hydroxy;
  amino;
  C$_{1-6}$alkylamino;
  N,N-di-(C$_{1-6}$alkyl)-amino;
  halo;
  halo-C$_{1-6}$alkyl;
  C$_{1-6}$alkylsulfonyl;
  C$_{1-6}$alkylsulfanyl;
  cyano; or
  —(CH$_2$)$_p$-A-C(O)—B—(CH$_2$)$_q$—R$^b$ wherein:

p and q each independently is 0 or 1;
A and B each independently is —O—, —NH— or a bond; and
$R^b$ is;
C$_{1-6}$alkyl;
C$_{1-6}$alkyloxy;
hydroxy;
amino;
C$_{1-6}$alkylamino;
N,N-di-(C$_{1-6}$alkyl)-amino;
halo-C$_{1-6}$alkyl; or
halo-C$_{1-6}$alkoxy;
$R^8$ is hydrogen or C$_{1-6}$alkyl;
$R^9$ and $R^{10}$ each is independently;
C$_{1-6}$alkyl;
C$_{1-6}$alkyloxy;
hydroxy;
amino;
C$_{1-6}$alkylamino;
N,N-di-(C$_{1-6}$alkyl)-amino;
halo;
halo-C$_{1-6}$alkyl;
halo-C$_{1-6}$alkoxy;
C$_{1-6}$alkylsulfonyl;
C$_{1-6}$alkylsulfanyl;
cyano; or
—(CH$_2$)$_p$-A-C(O)—B—(CH$_2$)$_q$—$R^b$ wherein:
p is 0 or 1;
q is 0 or 1;
A and B each independently is NR$^c$ or a bond, where R$^c$ is hydrogen or C$_{1-6}$alkyl; and
$R^b$ is C$_{1-6}$alkyl, C$_{1-6}$alkoxy or amino.

16. A compound of formula VI:

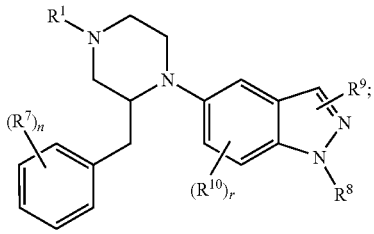

VI wherein:
n is from 0 to 2;
r is 0 or 1;
$R^1$ is hydrogen; or C$_{1-6}$alkyl;
each $R^7$ is independently:
C$_{1-6}$alkyl;
C$_{1-6}$alkyloxy;
hydroxy;
amino;
C$_{1-6}$alkylamino;
N,N-di-(C$_{1-6}$alkyl)-amino;
halo;
halo-C$_{1-6}$alkyl;
halo-C$_{1-6}$alkoxy;
C$_{1-6}$alkylsulfonyl;
C$_{1-6}$alkylsulfanyl;
cyano; or
—(CH$_2$)$_p$-A—C(O)—B—(CH$_2$)$_q$—$R^b$ wherein:
p and q each independently is 0 or 1;
A and B each independently is —O—, —NH— or a bond; and $R^b$ is;
C$_{1-6}$alkyl;
C$_{1-6}$alkyloxy;
hydroxy;
amino;
C$_{1-6}$alkylamino;
N,N-di-(C$_{1-6}$alkyl)-amino;
halo-C$_{1-6}$alkyl; or
halo-C$_{1-6}$alkoxy;
$R^8$ is hydrogen C$_{1-6}$alkyl;
$R^9$ and $R^{10}$ each is independently;
C$_{1-6}$alkyl;
C$_{1-6}$alkyloxy;
hydroxy
amino;
C$_{1-6}$alkylamino;
N,N-di-(C$_{1-6}$alkyl)-amino;
halo;
halo-C$_{1-6}$alkyl;
halo-C$_{1-6}$alkoxy;
C$_{1-6}$ alkylsulfonyl;
C$_{1-6}$alkylsulfanyl;
cyano; or
—(CH$_2$)$_p$-A-C(O)—B—(CH$_2$)$_q$—$R^b$;
p is 0 or 1;
q is 0 or 1;
A and B each independently is NR$^c$ or a bond, where R$^c$ is hydrogen or C$_{1-6}$alkyl; and
$R^b$ is C$_{1-6}$alkyl, C$_{1-6}$alkoxy or amino.

17. A pharmaceutical composition comprising a compound of claim 1 and a pharmaceutically acceptable carrier.

18. A method for treating depression, anxiety, or a combination thereof mediated by serotonin, norepinephrine or dopamine neurotransmission, or a combination thereof, said method comprising administering to a subject in need thereof an effective amount of a compound of claim 1.

19. A compound selected from the group consisting of:
6-(2-Benzyl-piperazin-1-yl)-1H-indole;
5-(2-Benzyl-piperazin-1-yl)-1-methyl-1H-indole;
4-(2-Benzyl-piperazin-1-yl)-1H-indole;
6-(2-Benzyl-piperazin-1-yl)-quinoline;
5-(2-Benzyl-piperazin-1-yl)-2,3-dihydro-1H-indole;
6-(2-Benzyl-piperazin-1-yl)-isoquinoline;
5-(2-Benzyl-piperazin-1-yl)-1H-indole-3-carbonitrile;
5-(2-Benzyl-4-methyl-piperazin-1-yl)-1H-indole;
5-(2-Benzyl-piperazin-1-yl)-1H-indole;
1-Benzo[b]thiophen-5-yl-2-benzyl-piperazine;
5-(2-Benzyl-piperazin-1-yl)-1H-pyrrolo[2,3-b]pyridine;
5-(2-Benzyl-piperazin-1-yl)-1H-indazole;
5-(2-Benzyl-piperazin-1-yl)-7-fluoro-1H-indole;
(S)-5-(2-Benzyl-piperazin-1-yl)-1H-indole;
(R)-5-(2-Benzyl-piperazin-1-yl)-1H-indole;
5-(2-Benzyl-piperazin-1-yl)-1H-indole-2-carboxylic acid amide;
(S)-5-(2-Benzyl-piperazin-1-yl)-1H-indazole;
(R)-5-(2-Benzyl-piperazin-1-yl)-1H-indazole;
1-Benzofuran-5-yl-2-benzyl-piperazine;
5-(2-Benzyl-piperazin-1-yl)-7-chloro-1H-indole;
5-(2-Benzyl-piperazin-1-yl)-7-methoxy-1H-indole;
5-[2-(3-Methoxy-benzyl)-piperazin-1-yl]-1H-indole;
5-[2-(3-Fluoro-benzyl)-piperazin-1-yl]-1H-indole;
5-[2-(3-Methyl-benzyl)-piperazin-1-yl]-1H-indole;
5-[2-(3-Trifluoromethoxy-benzyl)-piperazin-1-yl]-1H-indole;
5-[2-(3-Trifluoromethyl-benzyl)-piperazin-1-yl]-1H-indole;
5-[2-(4-Methoxy-benzyl)-piperazin-1-yl]-1H-indole;

5-(2-Benzyl-piperazin-1-yl)-2-methyl-1H-indole;
5-[2-(3-Methanesulfonyl-benzyl)-piperazin-1-yl]-1H-indole;
5-[2-(2-Methoxy-benzyl)-piperazin-1-yl]-1H-indole;
5-[2-(3-Methoxy-benzyl)-piperazin-1-yl]-1H-indazole;
5-[2-(3-Fluoro-benzyl)-piperazin-1-yl]-1H-indazole;
5-(2-Benzyl-piperazin-1-yl)-1-methyl-1H-indazole;
(S)-6-(2-Benzyl-piperazin-1-yl)-3-chloro-1H-indazole;
5-[2-(4-Methoxy-benzyl)-piperazin-1-yl]-1H-indazole;
(S)-6-(2-Benzyl-piperazin-1-yl)-3-methoxy-1,4-indazole;
4-[1-(1H-Indazol-5-yl)-piperazin-2-ylmethyl]-benzylamine;
(S)-5-(2-Benzyl-piperazin-1-yl)-1H-indole-2-carboxylic acid amide;
(R)-5-(2-Benzyl-piperazin-1-yl)-1H-indole-2-carboxylic acid amide;
5-(2-Benzyl-piperazin-1-yl)-1H-indole-3-carboxylic acid amide;
(R)-5-[2-(4-Methoxy-benzyl)-piperazin-1-yl]-1H-indazole;
(S)-5-[2-(4-Methoxy-benzyl)-piperazin-1-yl]-1H-indazole;
5-(2-Phenethyl-piperazin-1-yl)-1H-indole;
5-(2-Phenethyl-piperazin-1-yl)-1H-indazole;
(S)-5-(2-Phenethyl-piperazin-1-yl)-1H-indazole; and
(R)-5-(2-Phenethyl-piperazin-1-yl)-1H-indazole.

* * * * *